(12) United States Patent
Whalley et al.

(10) Patent No.: US 12,121,499 B2
(45) Date of Patent: *Oct. 22, 2024

(54) PHARMACEUTICAL COMPOSITION COMPRISING THE PHYTOCANNABINOIDS CANNABIDIVARIN (CBDV) AND CANNABIDIOL (CBD)

(71) Applicant: GW Pharma Limited, Cambridge (GB)

(72) Inventors: Benjamin Whalley, Cambridge (GB); Claire Williams, Cambridge (GB); Gary Stephens, Cambridge (GB); Thomas Hill, Cambridge (GB)

(73) Assignee: GW PHARMA LTD., Cambridgeshire (GB)

( * ) Notice: Subject to any disclaimer, the term of this patent is extended or adjusted under 35 U.S.C. 154(b) by 142 days.

This patent is subject to a terminal disclaimer.

(21) Appl. No.: 17/576,868

(22) Filed: Jan. 14, 2022

(65) Prior Publication Data

US 2022/0387347 A1 Dec. 8, 2022

Related U.S. Application Data

(63) Continuation of application No. 16/709,401, filed on Dec. 10, 2019, now Pat. No. 11,318,109, which is a continuation of application No. 14/345,968, filed as application No. PCT/GB2012/052284 on Sep. 14, 2012, now Pat. No. 10,729,665.

(30) Foreign Application Priority Data

Sep. 29, 2011 (GB) .................................... 1116789

(51) Int. Cl.
| | |
|---|---|
| A61K 31/05 | (2006.01) |
| A61K 31/045 | (2006.01) |
| A61K 31/352 | (2006.01) |
| A61K 31/353 | (2006.01) |
| A61K 36/185 | (2006.01) |
| A61K 45/06 | (2006.01) |

(52) U.S. Cl.
CPC ............ *A61K 31/05* (2013.01); *A61K 31/045* (2013.01); *A61K 31/352* (2013.01); *A61K 31/353* (2013.01); *A61K 36/185* (2013.01); *A61K 45/06* (2013.01)

(58) Field of Classification Search
CPC ..................................................... A61K 31/05
See application file for complete search history.

(56) References Cited

U.S. PATENT DOCUMENTS

| | | |
|---|---|---|
| 6,403,126 B1 | 6/2002 | Webster |
| 6,730,330 B2 | 5/2004 | Whittle et al. |
| 6,946,150 B2 | 9/2005 | Whittle |
| 6,949,582 B1 | 9/2005 | Wallace |
| 7,968,594 B2 | 6/2011 | Guy et al. |
| 8,293,786 B2 | 10/2012 | Stinchcomb |
| 8,632,825 B2 | 1/2014 | Diez et al. |
| 8,673,368 B2 | 3/2014 | Guy et al. |
| 8,790,719 B2 | 7/2014 | Parolaro et al. |
| 9,017,737 B2 | 4/2015 | Kikuchi et al. |
| 9,023,322 B2 | 5/2015 | Van Damme et al. |
| 9,066,920 B2 | 6/2015 | Whalley et al. |
| 9,095,554 B2 | 8/2015 | Lewis et al. |
| 9,125,859 B2 | 9/2015 | Whalley et al. |
| 9,168,278 B2 | 10/2015 | Guy et al. |
| 9,259,449 B2 | 2/2016 | Raderman |
| 9,474,726 B2 | 10/2016 | Guy et al. |
| 9,522,123 B2 | 12/2016 | Whalley et al. |
| 9,669,002 B2 | 6/2017 | Guy et al. |
| 9,675,654 B2 | 6/2017 | Parolaro et al. |

(Continued)

FOREIGN PATENT DOCUMENTS

| | | |
|---|---|---|
| CA | 2737447 A1 | 10/2012 |
| CA | 2859934 A1 | 3/2016 |

(Continued)

OTHER PUBLICATIONS

[No Author Listed] "Cannabidiol Therapy for Aicardi Syndrome" Aug. 2014, 4 pages.
[No Author Listed], "Missouri House passes cannabis extract legislation," Kansas City Star, 2014, https://kansascity.com/news/politics-government/article34674 7.html, 2 pages.
[No Author Listed], Cover and Table of Contents, J Pharmacology and Exp Therapeutics, Feb. 2010, 332(2), 4 pages.
Alger, "Not Too Excited? Thank Your Endocannabinoids," Neuron., Aug. 2006, 51(4):393-395.
American Epilepsy Society, Three Studies Shed New Light on the Effectiveness of Cannabis in Epilepsy, Oct. 14, 2014, 2 pages.
Ames et al., "Anticonvulsant effect of cannabidiol," S. Afr Med. J., Jan. 1986, 69(1):14.
Arain et al., "Pregabalin in the Management of Partial Epilepsy," Neuropsychiatr Dis Treat., Aug. 2009, 5:407-413.

(Continued)

*Primary Examiner* — Rei Tsang Shiao
(74) *Attorney, Agent, or Firm* — Cooley LLP

(57) ABSTRACT

This invention relates to a pharmaceutical composition comprising or consisting essentially of the phytocannabinoids cannabidivarin (CBDV) and cannabidiol (CBD). The composition is particularly safe and efficacious for use in the treatment of neurological conditions, characterized by hyper-excitability of the central nervous system, convulsions or seizures such as occur in epilepsy. Preferably the CBDV and the CBD are present with at least one non-cannabinoid component of cannabis such as one or more terpenes or a terpene fraction. More particularly the composition further comprises one or more cannabichromene type compounds. Particularly cannabichromene propyl variant (CBCV) and/or cannabichromene (CBC). More particularly still the composition is absent or substantially absent of other cannabinoids, including in particular tetrahydrocannabinol (THC) and tetrahydrocannabivarin (THCV), which would normally be present in significant amounts in cannabis chemotypes bred to contain a significant amount of CBDV and/or CBD.

22 Claims, 5 Drawing Sheets

(56) References Cited

U.S. PATENT DOCUMENTS

| | | |
|---|---|---|
| 9,730,911 B2 | 8/2017 | Verzura et al. |
| 9,949,936 B2 | 4/2018 | Guy et al. |
| 9,949,937 B2 | 4/2018 | Guy et al. |
| 9,956,183 B2 | 5/2018 | Guy et al. |
| 9,956,184 B2 | 5/2018 | Guy et al. |
| 9,956,185 B2 | 5/2018 | Guy et al. |
| 9,956,186 B2 | 5/2018 | Guy et al. |
| 9,962,341 B2 | 5/2018 | Stott et al. |
| 10,039,724 B2 | 8/2018 | Stott et al. |
| 10,092,525 B2 | 10/2018 | Guy et al. |
| 10,098,867 B2 | 10/2018 | Javid et al. |
| 10,111,840 B2 | 10/2018 | Guy et al. |
| 10,137,095 B2 | 11/2018 | Guy et al. |
| 10,220,005 B2 | 3/2019 | Martinez-Orgado |
| 10,226,433 B2 | 3/2019 | DiMarzo et al. |
| 10,583,096 B2 | 3/2020 | Guy et al. |
| 10,603,288 B2 | 3/2020 | Guy et al. |
| 10,653,641 B2 | 5/2020 | Robson et al. |
| 10,709,671 B2 | 7/2020 | Guy et al. |
| 10,709,673 B2 | 7/2020 | Guy et al. |
| 10,709,674 B2 | 7/2020 | Guy et al. |
| 10,729,665 B2 * | 8/2020 | Whalley .............. A61K 31/045 |
| 10,758,514 B2 | 9/2020 | Liu et al. |
| 10,765,643 B2 | 9/2020 | Guy et al. |
| 10,799,467 B2 | 10/2020 | Whalley et al. |
| 10,807,777 B2 | 10/2020 | Whittle |
| 10,849,860 B2 | 12/2020 | Guy et al. |
| 10,918,608 B2 | 2/2021 | Guy et al. |
| 10,966,939 B2 | 4/2021 | Guy et al. |
| 11,000,486 B2 | 5/2021 | Wright et al. |
| 11,065,209 B2 | 7/2021 | Guy et al. |
| 11,065,227 B2 | 7/2021 | Stott et al. |
| 11,096,905 B2 | 8/2021 | Guy et al. |
| 11,147,776 B2 | 10/2021 | Stott et al. |
| 11,147,783 B2 | 10/2021 | Stott et al. |
| 11,154,516 B2 | 10/2021 | Guy et al. |
| 11,154,517 B2 | 10/2021 | Wright et al. |
| 11,160,757 B1 | 11/2021 | Wilkhu et al. |
| 11,160,795 B2 | 11/2021 | Guy et al. |
| 11,207,292 B2 | 12/2021 | Guy et al. |
| 11,229,612 B2 | 1/2022 | Wright et al. |
| 11,291,631 B2 | 4/2022 | Shah |
| 11,311,498 B2 | 4/2022 | Guy et al. |
| 11,318,109 B2 * | 5/2022 | Whalley .............. A61K 31/353 |
| 11,357,741 B2 | 6/2022 | Guy et al. |
| 11,400,055 B2 | 8/2022 | Guy et al. |
| 11,413,266 B2 | 8/2022 | Biro et al. |
| 11,419,829 B2 | 8/2022 | Whalley et al. |
| 11,426,362 B2 | 8/2022 | Wright et al. |
| 11,446,258 B2 | 9/2022 | Guy et al. |
| 11,590,087 B2 | 2/2023 | Guy et al. |
| 11,633,369 B2 | 4/2023 | Guy et al. |
| 11,679,087 B2 | 6/2023 | Guy et al. |
| 11,684,598 B2 | 6/2023 | Stott et al. |
| 11,701,330 B2 | 7/2023 | Guy et al. |
| 11,766,411 B2 | 9/2023 | Guy et al. |
| 11,793,770 B2 | 10/2023 | Stott et al. |
| 11,806,319 B2 | 11/2023 | Wilkhu et al. |
| 11,865,102 B2 | 1/2024 | Guy et al. |
| 11,963,937 B2 | 4/2024 | Guy et al. |
| 2002/0137064 A1 | 9/2002 | Desprez et al. |
| 2003/0021752 A1 | 1/2003 | Whittle et al. |
| 2003/0158191 A1 | 8/2003 | Travis |
| 2003/0166727 A1 | 9/2003 | Mechoulam et al. |
| 2004/0039048 A1 | 2/2004 | Guzman Pastor et al. |
| 2004/0049059 A1 | 3/2004 | Mueller |
| 2004/0110828 A1 | 6/2004 | Chowdhury et al. |
| 2004/0138293 A1 | 7/2004 | Werner et al. |
| 2005/0042172 A1 | 2/2005 | Whittle |
| 2005/0165259 A1 | 7/2005 | Martin |
| 2005/0266108 A1 | 12/2005 | Flockhart et al. |
| 2006/0039959 A1 | 2/2006 | Wessling |
| 2006/0234273 A1 | 10/2006 | Desprez et al. |
| 2006/0247304 A1 | 11/2006 | Guy et al. |
| 2007/0060638 A1 | 3/2007 | Olmstead |
| 2007/0072938 A1 | 3/2007 | Rose |
| 2007/0203249 A1 | 8/2007 | Cercietti et al. |
| 2008/0057117 A1 | 3/2008 | Werner et al. |
| 2008/0119544 A1 | 5/2008 | Guy et al. |
| 2008/0188461 A1 | 8/2008 | Guan |
| 2008/0262099 A1 | 10/2008 | Whittle et al. |
| 2009/0264063 A1 | 10/2009 | Tinsley et al. |
| 2009/0306221 A1 | 12/2009 | Guy et al. |
| 2010/0239693 A1 | 9/2010 | Guy et al. |
| 2010/0317729 A1 | 12/2010 | Guy et al. |
| 2011/0028431 A1 | 2/2011 | Zerbe et al. |
| 2011/0038958 A1 | 2/2011 | Kikuchi et al. |
| 2011/0082195 A1 | 4/2011 | Guy et al. |
| 2011/0086113 A1 | 4/2011 | Velasco Diez et al. |
| 2011/0117216 A1 | 5/2011 | Velasco Diez et al. |
| 2012/0004251 A1 | 1/2012 | Whalley et al. |
| 2012/0165402 A1 | 6/2012 | Whalley et al. |
| 2012/0183606 A1 | 7/2012 | Bender et al. |
| 2012/0202891 A1 | 8/2012 | Stinchcomb et al. |
| 2012/0225136 A1 | 9/2012 | Whittle et al. |
| 2012/0270845 A1 | 10/2012 | Bannister et al. |
| 2013/0059018 A1 | 3/2013 | Parolaro et al. |
| 2013/0209483 A1 | 8/2013 | McAllister |
| 2013/0245110 A1 | 9/2013 | Guy et al. |
| 2013/0296398 A1 | 11/2013 | Whalley et al. |
| 2014/0100269 A1 | 4/2014 | Goskonda et al. |
| 2014/0155456 A9 | 6/2014 | Whalley et al. |
| 2014/0243405 A1 | 8/2014 | Whalley et al. |
| 2014/0287067 A1 | 9/2014 | Velasco Diez et al. |
| 2014/0335208 A1 | 11/2014 | Cawthorne et al. |
| 2014/0343044 A1 | 11/2014 | Ceulemens |
| 2015/0111939 A1 | 4/2015 | Gruening et al. |
| 2015/0181924 A1 | 7/2015 | Llamas |
| 2015/0313867 A1 | 11/2015 | Velasco Diez et al. |
| 2015/0320698 A1 | 11/2015 | Whalley et al. |
| 2015/0335590 A1 | 11/2015 | Whalley et al. |
| 2015/0343071 A1 | 12/2015 | Vangara |
| 2015/0359755 A1 | 12/2015 | Guy et al. |
| 2015/0359756 A1 | 12/2015 | Guy et al. |
| 2016/0136127 A1 | 5/2016 | Liu et al. |
| 2016/0166498 A1 | 6/2016 | Anastassov |
| 2016/0166514 A1 | 6/2016 | Guy et al. |
| 2016/0166515 A1 | 6/2016 | Guy et al. |
| 2016/0220529 A1 | 8/2016 | Guy et al. |
| 2016/0256411 A1 | 9/2016 | Aung-Din |
| 2017/0007551 A1 | 1/2017 | Guy et al. |
| 2017/0172939 A1 | 6/2017 | Guy et al. |
| 2017/0172940 A1 | 6/2017 | Guy et al. |
| 2017/0172941 A1 | 6/2017 | Guy et al. |
| 2017/0173043 A1 | 6/2017 | Guy et al. |
| 2017/0173044 A1 | 6/2017 | Guy et al. |
| 2017/0181982 A1 | 6/2017 | Guy et al. |
| 2017/0231923 A1 | 8/2017 | Guy |
| 2017/0239193 A1 | 8/2017 | Guy et al. |
| 2017/0246121 A1 | 8/2017 | Guy et al. |
| 2017/0266126 A1 | 9/2017 | Guy et al. |
| 2017/0273913 A1 | 9/2017 | Whalley et al. |
| 2018/0071210 A1 | 3/2018 | Wilkhu et al. |
| 2018/0228751 A1 | 8/2018 | Stott et al. |
| 2018/0338931 A1 | 11/2018 | Guy et al. |
| 2019/0083418 A1 | 3/2019 | Guy et al. |
| 2019/0099492 A1 | 4/2019 | Velasco Diez et al. |
| 2019/0167583 A1 | 6/2019 | Shah et al. |
| 2019/0175547 A1 | 6/2019 | Stott et al. |
| 2019/0314296 A1 | 10/2019 | Wright et al. |
| 2019/0321307 A1 | 10/2019 | Guy et al. |
| 2019/0365667 A1 | 12/2019 | Wright et al. |
| 2020/0138738 A1 | 5/2020 | Guy et al. |
| 2020/0179303 A1 | 6/2020 | Guy et al. |
| 2020/0206153 A1 | 7/2020 | Whalley et al. |
| 2020/0237683 A1 | 7/2020 | Whalley et al. |
| 2020/0297656 A1 | 9/2020 | Guy et al. |
| 2020/0352878 A1 | 11/2020 | Guy et al. |
| 2021/0015789 A1 | 1/2021 | Guy et al. |
| 2021/0052512 A1 | 2/2021 | Guy et al. |
| 2021/0059949 A1 | 3/2021 | Wilkhu et al. |
| 2021/0059960 A1 | 3/2021 | Wilkhu et al. |
| 2021/0059976 A1 | 3/2021 | Wilkhu et al. |
| 2021/0069333 A1 | 3/2021 | Velasco Diez et al. |

(56) References Cited

U.S. PATENT DOCUMENTS

| | | |
|---|---|---|
| 2021/0100755 A1 | 4/2021 | Whalley et al. |
| 2021/0169824 A1 | 6/2021 | Guy et al. |
| 2021/0177773 A1 | 6/2021 | Guy et al. |
| 2021/0290565 A1 | 9/2021 | Guy et al. |
| 2021/0308072 A1 | 10/2021 | Wright et al. |
| 2021/0330636 A1 | 10/2021 | Guy et al. |
| 2021/0401771 A1 | 12/2021 | Guy et al. |
| 2022/0000800 A1 | 1/2022 | Guy et al. |
| 2022/0008355 A1 | 1/2022 | Guy et al. |
| 2022/0016048 A1 | 1/2022 | Guy et al. |
| 2022/0023232 A1 | 1/2022 | Guy et al. |
| 2022/0040155 A1 | 2/2022 | Guy et al. |
| 2022/0062197 A1 | 3/2022 | Stott et al. |
| 2022/0062211 A1 | 3/2022 | Stott et al. |
| 2022/0087951 A1 | 3/2022 | Guy et al. |
| 2022/0096397 A1 | 3/2022 | Wright et al. |
| 2022/0168266 A1 | 6/2022 | Guy et al. |
| 2022/0183997 A1 | 6/2022 | Guy et al. |
| 2022/0184000 A1 | 6/2022 | Guy et al. |
| 2022/0202738 A1 | 6/2022 | Guy et al. |
| 2022/0211629 A1 | 7/2022 | Wilkhu et al. |
| 2022/0226257 A1 | 7/2022 | Guy et al. |
| 2022/0233495 A1 | 7/2022 | Silcock et al. |
| 2022/0249396 A1 | 8/2022 | Guy et al. |
| 2022/0257529 A1 | 8/2022 | Guy et al. |
| 2022/0265573 A1 | 8/2022 | Guy et al. |
| 2022/0288055 A1 | 9/2022 | Silcock et al. |
| 2022/0362149 A1 | 11/2022 | Shah |
| 2022/0378715 A1 | 12/2022 | Guy et al. |
| 2022/0378738 A1 | 12/2022 | Guy et al. |
| 2022/0395470 A1 | 12/2022 | Whalley et al. |
| 2022/0395471 A1 | 12/2022 | Guy et al. |
| 2023/0000789 A1 | 1/2023 | Guy et al. |
| 2023/0022487 A1 | 1/2023 | Guy et al. |
| 2023/0024312 A1 | 1/2023 | Whalley et al. |
| 2023/0026079 A1 | 1/2023 | Guy et al. |
| 2023/0032502 A1 | 2/2023 | Guy et al. |
| 2023/0038423 A1 | 2/2023 | Silcock et al. |
| 2023/0068885 A1 | 3/2023 | Guy et al. |
| 2023/0143812 A1 | 5/2023 | Knappertz et al. |
| 2023/0235825 A1 | 7/2023 | Thompson et al. |
| 2023/0248664 A1 | 8/2023 | Guy et al. |
| 2023/0263744 A1 | 8/2023 | Guy et al. |
| 2023/0277560 A1 | 9/2023 | Checketts et al. |
| 2023/0277561 A1 | 9/2023 | Checketts et al. |
| 2023/0277562 A1 | 9/2023 | Checketts et al. |
| 2023/0277563 A1 | 9/2023 | Checketts et al. |
| 2023/0285419 A1 | 9/2023 | Checketts et al. |
| 2023/0285420 A1 | 9/2023 | Checketts et al. |
| 2023/0285421 A1 | 9/2023 | Checketts et al. |
| 2023/0285422 A1 | 9/2023 | Checketts et al. |
| 2023/0285423 A1 | 9/2023 | Checketts et al. |
| 2023/0285424 A1 | 9/2023 | Checketts et al. |
| 2023/0285425 A1 | 9/2023 | Checketts et al. |
| 2023/0285426 A1 | 9/2023 | Checketts et al. |
| 2023/0285427 A1 | 9/2023 | Checketts et al. |
| 2023/0285428 A1 | 9/2023 | Checketts et al. |
| 2023/0301934 A1 | 9/2023 | Whalley et al. |
| 2023/0301936 A1 | 9/2023 | Guy et al. |
| 2023/0310464 A1 | 10/2023 | Checketts et al. |
| 2023/0346809 A1 | 11/2023 | Craig et al. |
| 2023/0372367 A1 | 11/2023 | Checketts et al. |
| 2023/0372368 A1 | 11/2023 | Checketts et al. |
| 2024/0016819 A1 | 1/2024 | Craig et al. |
| 2024/0025858 A1 | 1/2024 | Silcock et al. |
| 2024/0033229 A1 | 2/2024 | Guy et al. |
| 2024/0033272 A1 | 2/2024 | Checketts et al. |
| 2024/0043388 A1 | 2/2024 | Silcock et al. |
| 2024/0050452 A1 | 2/2024 | Craig et al. |
| 2024/0091241 A1 | 4/2024 | Guy et al. |
| 2024/0130981 A1 | 4/2024 | Wilkhu et al. |
| 2024/0131041 A1 | 4/2024 | Tse et al. |
| 2024/0165048 A1 | 5/2024 | Guy et al. |

FOREIGN PATENT DOCUMENTS

| | | |
|---|---|---|
| CN | 1976690 A | 6/2007 |
| CN | 101040855 A | 9/2007 |
| CN | 103110582 A | 5/2013 |
| DE | 102012-105063 A1 | 12/2013 |
| EP | 1 177 790 A1 | 2/2002 |
| EP | 1 802 274 B1 | 9/2008 |
| EP | 2448637 A1 | 5/2012 |
| GB | 2380129 A | 4/2003 |
| GB | 2384707 B | 8/2003 |
| GB | 2386322 A | 9/2003 |
| GB | 2391865 A | 2/2004 |
| GB | 2418612 A | 4/2006 |
| GB | 2434097 A | 7/2007 |
| GB | 2434312 A | 7/2007 |
| GB | 2439393 A | 12/2007 |
| GB | 2448535 A | 10/2008 |
| GB | 2450753 A | 1/2009 |
| GB | 2456183 A | 7/2009 |
| GB | 2460672 A | 12/2009 |
| GB | 2471523 A | 1/2011 |
| GB | 2471987 A | 1/2011 |
| GB | 2478595 A | 9/2011 |
| GB | 2479153 A | 10/2011 |
| GB | 2485291 A | 5/2012 |
| GB | 2471565 B | 7/2012 |
| GB | 2487183 A | 7/2012 |
| GB | 2478072 B | 12/2012 |
| GB | 2478074 B | 12/2012 |
| GB | 2492487 A | 1/2013 |
| GB | 2487712 B | 10/2015 |
| GB | 2531282 A | 4/2016 |
| GB | 2438682 A | 12/2017 |
| KR | 2012-0080675 A | 7/2012 |
| WO | WO 01/58445 A1 | 8/2001 |
| WO | WO 01/87295 A1 | 11/2001 |
| WO | WO-2002064109 A2 | 8/2002 |
| WO | WO 2002/069993 A1 | 9/2002 |
| WO | WO 2003/063847 A1 | 8/2003 |
| WO | WO-2003099302 A1 | 12/2003 |
| WO | WO-2004016246 A1 | 2/2004 |
| WO | WO-2004016277 A2 | 2/2004 |
| WO | WO 2004/041269 A2 | 5/2004 |
| WO | WO 2005/120478 A1 | 12/2005 |
| WO | WO 2006/037981 A1 | 4/2006 |
| WO | WO-2006054057 A2 | 5/2006 |
| WO | WO 2006/107903 A2 | 10/2006 |
| WO | WO-2006133941 A2 | 12/2006 |
| WO | WO 2007/052013 A1 | 5/2007 |
| WO | WO-2007083098 A1 | 7/2007 |
| WO | WO-2007138322 A1 | 12/2007 |
| WO | WO-2008019146 A2 | 2/2008 |
| WO | WO-2008094181 A2 | 8/2008 |
| WO | WO-2008129258 A1 | 10/2008 |
| WO | WO-2008144475 A1 | 11/2008 |
| WO | WO-2008021394 A2 | 12/2008 |
| WO | WO-2008146006 A1 | 12/2008 |
| WO | WO-2009007697 A1 | 1/2009 |
| WO | WO-2009007698 A1 | 1/2009 |
| WO | WO 2009/147438 A1 | 12/2009 |
| WO | WO 2009/147439 A1 | 12/2009 |
| WO | WO-2009020666 A1 | 12/2009 |
| WO | WO-2010012506 A1 | 2/2010 |
| WO | WO-2011001169 A1 | 1/2011 |
| WO | WO-2011121351 A1 | 10/2011 |
| WO | WO-2012033478 A1 | 3/2012 |
| WO | WO-2012093255 A1 | 7/2012 |
| WO | WO-2013032351 A1 | 3/2013 |
| WO | WO 2013/045891 A1 | 4/2013 |
| WO | WO-2014146699 A1 | 9/2014 |
| WO | WO-2015142501 A1 | 9/2015 |
| WO | WO 2015/198078 A | 12/2015 |
| WO | WO-2015184127 A2 | 12/2015 |
| WO | WO-2015193667 A1 | 12/2015 |
| WO | WO-2015193668 A1 | 12/2015 |
| WO | WO 2016/059404 A1 | 4/2016 |
| WO | WO-2016059405 A1 | 4/2016 |
| WO | WO 2016/084075 A1 | 6/2016 |

(56) References Cited

FOREIGN PATENT DOCUMENTS

| WO | WO 2016/087649 A2 | 6/2016 |
|---|---|---|
| WO | WO-2016118391 A1 | 7/2016 |
| WO | WO-2016147186 A1 | 9/2016 |
| WO | WO-2016022936 A1 | 11/2016 |
| WO | WO 2016/199148 A1 | 12/2016 |
| WO | WO-2017168138 A1 | 10/2017 |
| WO | WO 2018/002636 A1 | 1/2018 |
| WO | WO 2018/002637 A1 | 1/2018 |
| WO | WO 2018/037203 A1 | 3/2018 |

OTHER PUBLICATIONS

Arslan and Tirnaksiz, "Self-emulsifying Drug Delivery Systems," FABAD J Pharm Sci, 2013, 38(1):55-64.
Arzimanoglou et al., "All children who experience epileptic falls do not necessarily have Lennox-Gastaut syndrome . . . but many do," Epileptic Discord, 2011, 13:S3-S13.
AU Re-examination report—standard patent for Australian Patent No. 2012204800, dated May 3, 2019, 7 pages.
AU Third Party Observations for Application No. AU2012314129, dated Mar. 19, 2015, 51 pages.
Australian Office Action in Application No. 2012204800, dated Oct. 22, 2019, 5 pages.
Avoli et al., "Cellular and molecular mechanisms of epilepsy in the human brain," Prog Neurobiol., 2005, 77(3):166-200.
Bakhsm, "Key Attributes ofTKDL," Miftaah-al-Khazaain, 1930, 607-608 (with English translation).
Bancaud et al., "Proposal for Revised Clinical and Electroencephalographic Classification of Epileptic Seizures," Epilepsia, Aug. 1981, 22(4):489-501.
Banerjee et al., "Case Report: Aicardi syndrome: A report of five Indian cases," Neurology India, Mar. 2006, 54(1):91-93.
Barker-Haliski et al., "How Clinical Development Can, and Should. Inform Translational Science," Neuron, Nov. 2014, 84:582-593.
Benowitz and Jones, "Cardiovascular and metabolic considerations in prolonged cannabinoid administration in man," J Clin Pharm, 1981, 21:214S-223S.
Benowitz et al., "Metabolic and Psychophysiologic studies of cannabidiol hexobarbital interaction," ClinPharmacol Tuer., 1980, 28(1):115-120.
Bertram, "The Relevance of Kindling for Human Epilepsy," Epilepsia, Apr. 2007, 48(Suppl. 2):65-74.
Bhatt et al., "Indigenous Plants in Traditional Healthcare System in Kedarnath Valley of Western Himalaya," Indian J Tradit Knowl., Apr. 2008, 7(2):300-310.
Bhattacharyya et al., "Modulation of mediotemporal and ventrostriatal function in humans by Delta9-tetrahydrocannabinol: a neural basis for the effects of Cannabis sativa on learning and psychosis," Arch Gen Psychiatrv., 2009, 66:442-451.
BipolarHealthGroup.org [online], "Charlotte's Web Hemp Remedy," Bipolar Health Group, available on or before Sep. 6, 2017 , retrieved on May 21, 2018, URL <http:/bipolarhealthgroup.org/index.php/charlottes-web-hemp-remedy/>, 6 pages.
Booth et al., "Legalization's opening of medical pot research is dream and nightmare," Denver Post, Dec. 14, 2013, retrieved on Feb. 8, 2017, URL <https://www.denverpost.com/2013/12/14/legalizations-opening-of-medical-pot-research-is-dream-and-nightmare/>, 6 pages.
Bostanci et al., "The effects of octanol on penicillin induced epileptiform activity in rats: An in vivo study," Epilepsy Res., Jul. 27, 2006, 71(2-3):188-194.
Braida et al., "Post-ischemic treatment with cannabidiol prevents electroencephalographic flattening, hyper locomotion and neuronal injury in gerbils" Neuroscience Letters., 2003, 346:61-64.
Brodie et al., "Combining antiepileptic drugs—rational polytherapy?", Seizure, 2011, vol. 20, pp. 369-375.
Brust et al., "Marijuana use and the risk of new onset seizures," Trans Am Clin Climatol Assoc., 1992, 103:176-181.

Carlini et al., "Hypnotic and Antiepileptic Effects of Cannabidiol," J Clin Pharmacol., Aug.-Sep. 1981, 21(8-9 Sunnl):417S-427S.
Castel-Branco et al., "The Maximal Electroshock Seizure (MES) Model in the Preclinical Assessment of Potential New Antiepileptic Drugs," Methods Find Exp Clin Pharmacol., 2009, 31(2):101-106.
Charlotte's Web [online], "When to Expect Results from CW Hemp Oil", Mar. 13, 2017, retrieved on May 21, 2018, URL https://www.cwhemp.com/blog/expecting-results-from-hemp, 6 pages.
Charlotte's Web [online], "Whole-Plant Cannabinoids Outperform Single Molecule Compounds," CWHemp.com, Jan. 11, 2017, retrieved on Jun. 16, 2017, URL <https://www.cwhemp.com/blog/whole-plant-cw-hemp-cannabinoids>, 5 pages.
ChildNeurologyFoundation.org [online], "Disorder Directory: Learn from the Experts—LGS (Lennon-Gastaut Syndrome)," Child Neurology Foundation, available on or before Sep. 6, 2005, retrieved on May 21, 2018, URL http://www.childneurologyfoundation.org/disorders/lgs-lennox-gastaut-syndrome, 10 pages.
Chiron and Dulac, "The Pharmacologic Treatment ofDravet Syndrome," Epilepsia, 2011, 52(Suppl. 2):72-75.
Chiu et al., "The Influence ofCannabidiol and 9-Tetrahydrocannabinol on Cobalt Epilepsy in Rats," Epilepsia., 1979, 20:365-375.
Conry et al., "Clobazam in the treatment ofLennox-Gastaut syndrome," Epilepsia, May 2009, 50(5):1158-1166.
Consroe and Sandyk, "Chapter 12: Potential Role ofCannabinoids for Therapy of Neurological Disorders," Marijuana/ Cannabinoids: Neurobiology and Neurophysiology, ed. L. Murphy, 1992, 459-524.
Consroe et al., "Anticonvulsant drug antagonism of 9tetrahydrocannabinol-induced seizures in rabbits," Res Commun Chem Pathol Pharmacol., Jan. 1977, 16(1):1-13.
Consroe et al., "Anticonvulsant Interaction ofCannabidiol and Ethosuximide in Rats," J. Pharm. Pharmac., Aug. 1977, 29(8):500-501.
Consroe et al., "Anticonvulsant Nature ofMarihuana Smoking," JAMA, Oct. 1975, 234(3):306-307.
Consroe et al., "Cannabidiol—Antiepileptic Drug Comparisons and Interactions in Experimentally Induced Seizures in Rats," J. Pharm. Exp. Therap., Apr. 1977, 201(1):26-32.
Consroe et al., "Controlled clinical trial of cannabidiol in Huntington's Disease," Pharmacology, Biochemistry & Behavior, 1991, 40:701-708.
Consroe et al., "Effects of Cannabidiol on Behavioral Seizures Caused by Convulsant Drugs or Current in Mice," Eur J Pharm, Sep. 1982, 83(3-4):293-298.
Consroe et al., "Chapter 2: Therapeutic Potential ofCannabinoids in Neurological Disorders," Cannabinoids as Therapeutic Agents, R. Mechoulam ed., 1986, 21-49.
Cortesi et al., "Potential therapeutical effects of cannabidiol in children with pharmacoresistant epilepsy," Med Hypotheses., 2007, 68(4):920-921.
Cortez and Snead, "Chapter 10: Pharmacologic Models of Generalized Absence Seizures in Rodents," Models of Seizures and Epilepsy, 2006, 111-126.
Crespel, et al., "Chapter 14: Lennox-Gastaut Syndrome," Epileptic Syndromes in Infancy, Childhood, and Adolescence, 2012, 5th Edition, ed. M. Bureau, 189-216.
Cunha et al., "Chronic Administration ofCannabidiol to Healthy Volunteers and Epileptic Patients," Pharmacology, 1980. 21(3):175-185.
Curia et al., "The pilocarpine model of temporal lobe epilepsy," J Neuroscience Methods, Jul. 2008, 172(2-4):143-157.
Czapinski et al., "Mar. 17, 2008: Randomized 36-month comparative study ofvalproic acid (VPA), phenytoin (PHT), phenobarbital (PB) and carbamazepine (CBZ) efficacy in patients with newly diagnosed epilepsy with partial complex seizures," J. Neurol. Sci., Sep. 1997, 150(1):S162-SI63.
Dasa et al., "Key Attributes ofTKDL: Ganja," Brhat Nighantu Ratnakara (Saligramanighantubhusanam), 1997, 6 pages (with English translation).
Davis and Ramsey, "Antiepileptic action ofmarihuana-active substances," Federation Proceedings., Mar. 1949, 8:284-285.
Davis et al., "A Predominant Role for Inhibition of the Adenylate Cyclase/Protein Kinase A Pathway in ERK Activation by Can-

(56) References Cited

OTHER PUBLICATIONS nabinoid Receptor 1 in NIE-115 Neuroblastoma Cells," J Biol Chem., Dec. 2003, 278(49):48973-48980.
De Meijer, "Chapter 5: The Chemical Phenotypes (Chemotypes) of Cannabis," Handbook of Cannabis, ed. Roger G. Pertwee, 2014, 89-110.
De Oliveira, et al., "Anticonvulsant activity of P-caryophyllene against pentylenetetrazol-induced seizures," Epilepsy Behav, Mar. 2016, 56:26-31.
Deshpande et al., "Cannabinoid CBI Receptor Antagonists Cause Status Epilepticus-like Activity in the Hippocampal Neuronal Culture Model of Acquired Epilepsy," Neurosci Lett., Jan. 2007, 411:11-16.
Devinsky et al., "Cannabidiol: Pharmacology and potential therapeutic role in epilepsy and other neuropsychiatric disorders," Epilepsia, 2014, 55(6):791-802.
Dravet, "The core Dravet syndrome phenotype," Epilepsia, Apr. 2011, 52(Suppl 2):3-9.
Dreifus et al., "Proposal for Revised Clinical and Electroencephalographic Classification of Epileptic Seizures," Epilepsia, Aug. 1981, 22:489-501.
Dulac and Kaminska, "Use ofLamotrigine in Lennox-Gastaut and Related Epilepsy Syndromes," J. Child Neurolog., Nov. 1997, 12(SI):S23-S29.
Dulac et al., "Vigabatrin in Childhood Epilepsy," J. Child Neurolog., 1991, 6(S2):S30-S37.
Eadie, "Shortcomings in the current treatment of epilepsy," Expert Rev Neurother., Dec. 2012, 12(12):1419-1427.
Eggers, "Temporal lobe epilepsy is a disease of faulty neuronal resonators rather than oscillators, and all seizures are provoked, usually by stress," Med Hypotheses, 2007, 69(6): 1284-1289.
Engel et al., "Chapter 1: What Should be Modeled?," In Models Seizure Epilepsy., 2006, 14 pages.
Engel, "Report of the ILAE Classification Core Group," Epilepsia, 2006, 47(9):1558-1568.
EPO Annex to the Communication in Opposition for European Appln. No. 10734541.5, dated Jan. 28, 2016, 5 pages.
EPO Auxiliary Requests to the File in European Patent No. EP2448637, dated Nov. 2, 2016, 45 pages.
EPO Communication ofa Notice of Opposition in European Appln. No. 10734541.5, dated Dec. 17, 2014, 1 page.
EPO Communication Pursuant to Article 94(3) EPC in European Appln. No. 10734541.5, dated Oct. 23, 2012, 3 pages.
EPO Interlocutory Decision in Opposition in European Appln. No. EP2448637, dated Dec. 15, 2016, 91 pages.
EPO Letter from Opponent Regarding Oral Proceedings in European Patent No. EP2448637, dated Oct. 20, 2016, 6 pages.
EPO Notice of Appeal in European Patent No. EP2448637, dated Feb. 14, 2017, 5 pages.
EPO Notice of Opposition to a European Patent No. EP2448637, Dated Dec. 5, 2014, 20 pages.
EPO Opponent Response to the Preliminary Opinion of the Opposition Division in European Patent No. EP2448637, dated Jun. 23, 2016, 27 pages.
EPO Opponent Response to the Preliminary Opinion of the Opposition Division in European Patent No. EP2448637, dated Sep. 9, 2016, 25 pages.
EPO Opponent Response to the Written Submissions in European Patent No. EP2448637, dated Oct. 12, 2016, 18 pages.
EPO Opponent Response to the Written Submissions in European Patent No. EP2448637, dated Oct. 20, 2016, 3 pages.
EPO Opponent Written Submission in European Patent No. EP2448637, dated Nov. 4, 2016, 3 pages.
EPO Opposition, Expert Statement of Dr. Emma Louise Cheetham in European Appln. No. EP10734541.5, dated Nov. 4, 2016, 1 pages.
EPO Opposition, Expert Statement of Professor Anthony G Marson in European Appln. No. EP10734541.5, dated Jun. 14, 2016, 9 pages.
EPO Opposition, Expert Statement of Professor Benjamin J. Whalley in European Appln. No. EP10734541.5, dated Sep. 9, 2016, 11 pages.
EPO Opposition, Expert Statement of Vincenzo Di Marzo in European Appln. No. EP10734541.5, dated Sep. 9, 2016, 10 pages.
EPO Opposition, Supplemental Expert Statement of Professor Benjamin J. Whalley, dated Nov. 4, 2016, 9 pages.
EPO Reply of the Patent Proprietor to the Notice(s) of Opposition in European Patent No. 2448637, dated May 28, 2015, 12 pages.
EPO Reply to Examination Report in European Patent Application No. 10734541.5, dated Feb. 15, 2013, 54 pages.
EPO Reply to Opponent's Written Submission in European Patent No. EP2448637, dated Nov. 4, 2016, 13 pages.
EPO Reply to Opponent's Written Submissions in European Patent No. EP2448637, dated Oct. 18, 2016, 5 pages.
EPO Reply to Preliminary Opinion and Opponent's Observations in European Patent No. EP2448637, dated Sep. 9, 2016, 65 pages.
EPO Reply to Proprietor's Statement of Grounds of Appeal in European Patent No. EP2448637, dated Sep. 8, 2017, 5 pages.
EPO Response to the Statement of Grounds of Appeal in European Patent No. 2448637, dated Sep. 5, 2017, 17 pages.
EPO Statement of Grounds of Appeal in European Appln. No. 10734541.5 , dated Apr. 21, 2017, 14 pages.
EPO Statement of Grounds of Appeal in European Appln. No. 10734541.5, dated Apr. 12, 2017, 6 pages.
EPO Statement of Opposition in European Appln. No. EP10734541.5, dated Dec. 5, 2014, 14 pages.
EPO Third Party Observations in European Appln. No. EP10734541.5, dated Apr. 3, 2017, 19 pages.
EPO Third Party Observations in European Appln. No. EP11712658.1, dated Nov. 22, 2013, 14 pages.
Fariello, "Parenteral Penicillin in Rats: An Experimental Model ofMultifocal Epilepsy," Epilepsia, 1976, 17:217-222.
FDA [online], "Warning Letters and Test Results for Cannabidiol-Related Products," 2015 Warning Letters, retrieved on Nov. 14, 2017, URL <https://www.fda.gov/newsevents/publichealthfocus/ucm484109.htm>, 4 pages.
Fda, Guidance for Industry: Estimating the maximum Safe Starting Dose in Initial Clinical Trials for Therapeutics in Adult Healthy Volunteers, U.S. Dept of Health and Human Services: Food and Drug Administration, Jul. 2005, 30 pages.
Ferdinand et al., "Cannabis-Psychosis Pathway Independent of Other Types of Psychopathology," Schizophrenia Research, 2005, 79:289-295.
Fisher et al., "The impact of epilepsy from the patient's perspective I. Descriptions and subjective perceptions," Epilepsy Research, 2000, 41(1):39-51.
Friedman et al., "Cannabinoids in the Treatment of Epilepsy", New England Journal of Medicine, 2015, vol. 373, nn. 1048-1058.
Gabor et al., "Lorazepam Versus Phenobarbital: Candidates for Drug of Choice for Treatment of Status Epilepticus," J Epilepsy, Jan. 1990, 3(1):3-6.
Gallily et al., "Overcoming the Bell-Shaped Dose-Response of Cannabidiol by Using Cannabis Extract Emiched in Cannabidiol," Pharmacology & Pharmacy, Jan. 2015, 6:75-85.
Gardner [online], "Comes Now Epidiolex (FDA Approves IND Studies ofCBD)," BeyondTHC.com, Oct. 22, 2013, retrieved on Jan. 31, 2018, URL <http://www.beyondthc.com/comes-now-epidiolex-fda-annroves-ind-studies-of-cbd>, 4 pages.
Gastaut., "Clinical and Electroencephalographical Classification of Epileptic Seizures," Epilepsia, 1970, 11:102-113.
Gaston et al., "Interactions between cannabidiol and commonly used antiepileptic drugs" Epilepsia, 2017, vol. 58, No. 9, pp. 1586-1592.
GB Combined Search and Examination Report in GB Appln. No. GBI 16789.7, dated Jan. 4, 2012, 8 pages.
GB Combined Search and Examination Report in Application No. GB1611544.6, dated Mar. 29, 2017, 8 pages.
GB Combined Search and Examination Report in GB Appln. No. GBI 100043.7, dated Mar. 25, 2011, 8 pages.
GB Combined Search and Examination Report in GB Appln. No. GBI 121919.3, dated Feb. 29, 2012, 8 pages.

(56) References Cited

OTHER PUBLICATIONS

GB Combined Search and Examination Report in GB Appln. No. GB1410771.8, dated Feb. 27, 2015, 7 pages.
GB Combined Search and Examination Report in GB Appln. No. GB1414813.4, dated Sep. 5, 2014, 8 pages.
GB Combined Search and Examination Report in GB Appln. No. GB1418166.3, dated Jul. 2, 2015, 8 pages.
GB Combined Search and Examination Report in GB Appln. No. GB1418170.5, dated Jul. 2, 2015, 6 pages.
GB Combined Search and Examination Report in GB Appln. No. GB1418171.3, dated Jun. 29, 2015, 8 pages.
GB Combined Search and Examination Report in GB Appln. No. GB1506550.1, dated Feb. 5, 2016, 9 pages.
GB Combined Search and Examination Report in GB Appln. No. GB1514079.1, dated May 4, 2016, 9 pages.
GB Combined Search and Examination Report in GB Appln. No. GB1605448.8, dated Jan. 12, 2017, 6 pages.
GB Combined Search and Examination Report in GB Appln. No. GB1621480.1, dated Sep. 22, 2017, pages.
GB Examination Report in GB Appln. No. GB100043.7, dated Mar. 18, 2014, 2 pages.
Gedde [online], "Clinical Experience with Cannabis in Treatment-Resistant Pediatric Epilepsy," Marijuana for Medical Professionals Conference, Sep. 9-11, 2014, URL <http://www.theroc.us/images/gedde presentation.pdf, Sep. 9-11, 2014>, 45 pages.
Gedde et al., "3.330: Whole Cannabis Extract of High Concentration Cannabidiol May Calm Seizures in Highly Refractory Pediatric Epilepsies," American Epilepsy Society, Dec. 2013, 449-450.
Geffrey et al., "Cannabidiol (CBD) Treatment for Refractory Epilepsy," American Epilepsy Society, Annual Meeting Abstract 2.427, 2014, retrieved on Feb. 10, 2017, URL <https://www.aesnet.org/meetings events/annual meeting abstracts/view/1868979>, 2 pages.
Gloss, D., Vickrey, B.: "Cannabinoids for epilepsy (Review)", Cochrane Database of Systematic Reviews, 2014, 3, Art. No. CD009270, 25 pages.
Green [online], "CBD: An Unconventional Therapy," Nugs.com, Mar. 24, 2014, URL <http://nugs.com/article/cbd-an-unconventional-therapy.html>, 5 pages.
Gresham et al., "Treating Lennox-Gastaut syndrome in epileptic pediatric patients with third generation rufmamide," Neuropsychiatr Dis Treat, Oct. 5, 2010, 6:639-645.
Gross et al., "Marijuana use and Epilepsy: Prevalence in Patients of a Tertiary Care Epilepsy Center," Neurology, Jun. 8, 2004, 62(11):2095-2097.
Grotenhermen, "Epilepsiebehandlung des Angelman-Syndroms mit CBD (Cannabidiol) (Epilepsy treatment of Angelman syndrome with CBD (cannabidiol))," Angelman e.V., Jan. 2015, retrieved on Jun. 7, 2019, URL <http://s8a85e4d6fcfb04b6.jimcontent.com/download/version/1472724876/module/9873059694/name/Epilepsiebehandlung%20durch%20CBD.pdf>, 8 pages (with Machine translation).
Guerrini et al., "Lamotrigine and Seizure Aggravation in Severe Myoclonic Epilepsy," Epilepsia, 1998, 39(5):508-512.
Guimaraes et al., "Antianxiety effect of cannabidiol in the elevated plus-maze," Psychopharmacolo, 1990, 100: 558-559.
GWPharm [online], "GW Pharmaceuticals Announces Epidiolex(R) Receives Fast Track Designation from FDA for the Treatment ofDravet Syndrome," GW Pharmaceuticals Press Release, Jun. 6, 2014, retrieved on Mar. 1, 2017, URL <https://www.gwpharm.com/about-us/news/gw-pharmaceuticals-announces-epidiolex%C2%AE-receives-fast-track-designation-fda-treatment>, 2 pages.
GWPharm [online], "GW Pharmaceuticals Announces Physician Reports ofEpidiolex(R) Treatment Effect in Children and Young Adults with Treatment-resistant epilepsy from Physician-Led Expanded Access Treatment Program," GW Pharmaceuticals Press Release, Jun. 17, 2014, retrieved on May 1, 2017, URL <https://www.gwpharm.com/about-us/news/gw-pharmaceuticals-announces-physician-reports-epidiolex%C2%AE-treatment-effect-children>, 8 pages.
GWPharm [online], "GW Pharmaceuticals Announces Preliminary Results of Phase 2a Study for its Pipeline Compound GWP42006," GW Pharmaceuticals Press Release, Feb. 21, 2018, retrieved on Jun. 29, 2018, URL <https://www.gwpharm.com/about-us/news/gw-pharmaceuticals-announces-preliminarv-results-phase-2a-studv-its-pipeline-compound>, 5 pages.
GWPharm [online], "GW Pharmaceuticals Provides Update on Orphan Program in Childhood Epilepsy for Epidiolex®," GW Pharmaceuticals Press Release, Nov. 15, 2013, retrieved on Jun. 20, 2018, URL <https://www.gwpharm.com/about-us/news/gw-pharmaceuticals-provides-update-orphan-program-childhood-epilepsy-epidiolex%C2%AE>, 5 pages.
GWPharm [online], "GW Pharmaceuticals Receives Orphan Drug Designation by FDA for Epidiolex® in the Treatment ofLennox-Gastaut Syndrome," GW Pharmaceuticals Press Release, Feb. 28, 2014, retrieved on Feb. 10, 2017, URL <https://www.gwpharm.com/about-us/news/gw-pharmaceuticals-receives-orphan-drug-designation-fda-epidiolex%C2%AE-treatment-lennox>, 4 pages.
GWPharm [online], "Orphan Drug Designation Granted for Epidiolex in Dravet syndrome by the FDA-Seven Expanded Access INDs granted by FDA to US physicians to treat with Epidiolex 125 children suffering from intractable epilepsy syndromes," GW Pharmaceuticals Press Release, Nov. 15, 2013, retrieved on Feb. 10, 2017, URL <https://www.gwpharm.com/about-us/news/gw-pharmaceuticals-provides-update-orphan-program-childhood-epilepsy-epidiolex%C2%AE>, 5 pages.
Heinemann et al., "Chapter 4: An Overview ofIn Vitro Seizure Models in Acute and Organotypic Slices," Models of Seizures and Epilepsy, 2006, 35-44.
Hill et al., "Cannabidivarin is anticonvulsant in mouse and rat," Br J Pharmacol, Dec. 2012, 167(8):1629-1642.
Hill et al., "Li9-Tetrahydrocannabivarin suppresses in vitro epileptiform and in vivo seizure activity in adult rats," Epilepsia, Aug. 2010, 51(8):1522-1532.
Hill, "Cannabidivarin-rich cannabis extracts are anticonvulsant in mouse and rat via a CB1 receptor-independent mechanism," British Journal of Pharmacology, Oct. 2013, 170(3):679-692.
Holmes et al. "Choosing the Correct AED: From Animal Studies to the Clinic, "Pediatr Neurol, Mar. 2008, 38(3):151-162.
Iannotti et al., "Nonpsychotropic plant cannabinoids, cannabidivarin (CBDV) and cannabidiol (CBD), activate and desensitize transient receptor potential vanilloid 1 (TRPVI) channels in vitro: Potential for the treatment ofneuronal hyperexcitability," ACS Chem. Neurosci., Jul. 16, 2014, 5:1131-1141.
ICE Epilepsy Alliance, The Dravet Syndrome Spectrum, Nov. 2008, 2 pages.
*Insys Development Company, Inc.* v. *GW Pharma Limited and Otsuka Pharmaceutical Co., Ltd.*, Decision in IPR2017-00503, U.S. Pat. No. 9,066,920, dated Jul. 7, 2017, 26 pages.
*Insys Development Company, Inc.* v. *GW Pharma Limited and Otsuka Pharmaceutical Co., Ltd.*, Declaration by Mark Polyakov, IPR2017-00503, U.S. Pat. No. 9,066,920, dated May 29, 2018, 1 page.
*Insys Development Company, Inc.* v. *GW Pharma Limited and Otsuka Pharmaceutical Co., Ltd.*, Declaration of Professor Anthony G. Marson in IPR2017-00503, U.S. Pat. No. 9,066,920, dated Dec. 13, 2016, 28 pages.
*Insys Development Company, Inc.* v. *GW Pharma Limited and Otsuka Pharmaceutical Co., Ltd.*, Declaration of Professor H. Steve White in IPR2017-00503, U.S. Pat. No. 9,066,920, dated Oct. 24, 2017, 69 pages.
*Insys Development Company, Inc.* v. *GW Pharma Limited and Otsuka Pharmaceutical Co., Ltd.*, Declaration of Professor Leslie Benet in IPR2017-00503, U.S. Pat. No. 9,066,920, dated Nov. 22, 2016, 18 pages.
*Insys Development Company, Inc.* v. *GW Pharma Limited and Otsuka Pharmaceutical Co., Ltd.*, Deposition ofH. Steve White, dated Dec. 13, 2016, 50 pages.
*Insys Development Company, Inc.* v. *GW Pharma Limited and Otsuka Pharmaceutical Co., Ltd.*, Final Written Decision in IPR2017-00503, U.S. Pat. No. 9,066,920, dated Jan. 3, 2019, 40 pages.

(56) References Cited

OTHER PUBLICATIONS

*Insys Development Company, Inc. v. GW Pharma Limited and Otsuka Pharmaceutical Co., Ltd.*, Patent Owners' Preliminary Response in IPR2017-00503, U.S. Pat. No. 9,066,920, dated Apr. 11, 2017, 45 pages.
*Insys Development Company, Inc. v. GW Pharma Limited and Otsuka Pharmaceutical Co., Ltd.*, Petition for Inter Partes Review, IPR2017-00503, U.S. Pat. No. 9,066,920, dated Dec. 16, 2016, 78 pages.
*Insys Development Company, Inc. v. GW Pharma Limited and Otsuka Pharmaceutical Co., Ltd.*, Petitioner's Brief Regarding Ground III of the IPR, IPR2017-00503, U.S. Pat. No. 9,066,920, dated May 29, 2018, 45 pages.
*Insys Development Company, Inc. v. GW Pharma Limited and Otsuka Pharmaceutical Co., Ltd.*, Petitioner's Reply to Patent Owner's Response, IPR2017-00503, U.S. Pat. No. 9,066,920, dated Jun. 19, 2018, 6 pages.
IUPHAR/BPS Guide to Pharmacology [online], "Entry for A9-tetrahydrocannabidiol," available on or before Mar. 29, 2016, retrieved on Jun. 20, 2018, URL <http://www.guidetopharmacology.org/GRAC/LigandDisplayForward?tab=biology&ligandid=242>, 2 pages.
Iuvone et al., "Neuroprotective Effect of Cannabidiol, a Non-psychoactive Component From Cannabis Sativa, on -amyloid-induced toxicity in PC12 Cells," J Neurochem, Apr. 2004, 89(1):134-41.
Izzo et al., "Non-psychotropic plant cannabinoids: new therapeutic opportunities from an ancient herb," Trends in Pharmacological Sciences, 2009, 30(10):515-527.
Jacobson and Porter, "Survey of Current Cannabidiol use in Pediatric Treatment-Resistant Epilepsy", Apr. 2013, URL <https://www.thcint.com/uploads/1/9/3/7/19371199/cannabidiol use in oediatric epilepsy.pdt>, 1 page.
Jeavons et al., "Sodium Calproate in Treatment of Epilepsy," Br Med J., Jun. 15, 1974, 2(5919):584-586.
Jones et al. [online], Info & Metrics/ Article Information,"Cannabidiol Displays Antiepileptiform and Antiseizure Properties in Vitro and in Vivo," J Pharmacol Exp Tuer., Feb. 2010, 332(2): 569-577, retrieved on Jun. 25, 2018, URL: http://jpet.aspetjournals.org/content/332/2/569/tab-article-info, 9 pages.
Jones et al., "Cannabidiol Displays Antiepileptiform and Antiseizure Properties in Vitro and in Vivo," J Pharmacol Exo Ther., Feb. 2010, 332(2):559-577.
Joy et al., "Marijuana and Medicine: Assessing the Science Base", Institute of Medicine, National Academy Press, 1999, 170 pages.
Kahan et al., "Risk of Selection Bias in Randomized Trials," Trials, Sep. 2015, 16:405, 7 pages.
Kaplan, "F.D.A. Panel Recommends Approval of Cannabis-Based Drug for Epilepsy," NY Times, Apr. 19, 2018, retrieved on Jun. 20, 2018, URL <https://www.nytimes.com/2018/04/19/health/epidiolex-fda-cannabis-maraiuana.html>, 3 pages.
Karler et al., "The anticonvulsant activity of cannabidiol and cannabinol," Life Science, 1973, 13:1527-1531.
Karler et al., "The Cannabinoids as Potential Antiepileptics," J Clin Pharmacol., Aug.-Sep. 1981, 21:437S-448S.
Kelley et al., "Doose syndrome (myoclonic-astatic epilepsy): 40 years of progress," Developmental Medicine & Child Neurology, Aug. 2010, 52:988-993.
Khan et al., "Key Attributes of TKDL: Laooq-e-Qinnab/Barai Zeequn-Nafs," Khazaain-al-Advia, 1911, 2 pages (with English translation).
Khan et al., "Key Attributes of TKDL: Nuskha-e-Qutoor," Muheet-e-Azam, 1887, 2 pages (with English translation).
Khan et al., "Key Attributes of TKDL: Sufoof-e-qinnab Barae Waja," Khazaain-al-Adiva, 1911, 5 pages (with English translation).
Khan et al., "Key Attributes of TKDL: Usaara-e-Qinnab Barai Qoolanj," Khazaain-al-Advia, 1911, 6 pages (with English translation).
Khan et al., "Key Attributes of TKDL: Zimad-e-qinnab," Khazaain-al-Adiva, 1911, 5 pages (with English translation).
Klitgaard et al., "Electrophysiological, neurochemical and regional effects oflevetiracetam in the rat pilocamine model of temporal lobe epilepsy," Seizure, Mar. 2003, 12(2):92-100.
Klitgaard et al., "Evidence for a unique profile of levetiracetam in rodent models of seizures and epilepsy," European J Pharm, Jul. 1998, 353(2):191-206.
Koppel et al.: "Systematic review: Efficacy and safety of medical marijuana in selected neurologic disorders" American Academy of Neurology, 2014, vol. 82, nn. 1556-1563.
Kramer et al., "Febrile infection-related epilepsy syndrome (FIRES): pathogenesis, treatment, and outcome: a multicenter study on 77 children," Epilepsia, Nov. 2011, 52(11):1956-1965.
Kruk-Slomka et al., "A comparison of mecamylamine and bupropion effects on memory-related responses induced by nicotine and scopolamine in the novel object recognition test in mice," Pharmacological Reports, Aug. 2014, 66(4):638-646.
Kurz and Blass, "Use of dronabinol (delta-9-THC) in autism: a prospective single-case- study with an early infantile autistic child," 2010, Cannabinoids, 5(4):4-6.
Kwan et al., "Defmition of drug resistant epilepsy: consensus proposal by the ad hoc Task Force of the ILAE Commission on Therapeutic Strategies," Epilepsia, Jun. 2010, 51(6):1069-1077.
LaPrairie et al., "Cannabidiol is a negative allosteric modulator of the cannabidinoid CB1 receptor," British J Pharmacology, 2015, 172(20): 4790-4805.
LeafScience.com [online], "What are the Highest CBD Strains?" Oct. 15, 2014, retrieved on Feb. 16, 2017, URL <www.leafscience.com/2014/10/15/hi!! hest-cbd-strains/>, 2 pages.
Leo et al., "Cannabidiol and epilepsy: Rationale and therapeutic potential," Pharamacological Research, Mar. 2016, 107: 85-92.
Lewis, "Mystery Mechanisms," TheScientist.com, Jul. 29, 2016, retrieved on Nov. 8, 2017, URL <https://www.the-scientist.com/?articles.view/articleNo/46688/title/Mystery-Mechanisms/>, 2 pages.
Lieu et al., "Assessment of self-selection bias in a pediatric unilateral hearing loss study," Otolaryngol Head Neck Surg, Mar. 2010, 142(3):427-433.
Lindamood and Colasanti, "Effects of f,,,9-Tetrahydrocannabinol and Cannabidiol on Sodium-Dependent High Affmity Choline Uptake in the Rat Hippocampusl," J Pharmacology Experimental Therapeutics, 1980, 213(2):216-221.
Long et al., "The Pharmacological actions of cannabidiol," Drugs of the Future, Jul. 2005, 30(7):747-753.
Loscher and Schmidt, "Modem antiepileptic drug development has failed to deliver: ways out of the current dilemma." Epilepsia, Apr. 2011, 52(4):657-78.
Lowenstein "Chapter 363: Seizures and Epilepsy," Diseases of the Central Nervous System, 2008, 2498-2512.
Luttjohann et al., "A Revised Racine's scale for PTZ-induced seizures in rats," Physiology & Behavior, 2009, 98:579-586.
Lutz, "On-demand activation of the endocannabinoid system in the control of neuronal excitability and epileptiform seizures," Biochemical Pharmacology, Nov. 2004, 68(9):1691-1698.
Maa et al., "The Case for Medical Marijuana in Epilepsy," Epilepsia, Jun. 2014, 55(6):783-786.
Mackie, "Cannabinoid Receptors as Therapeutic Targets," Annu Rev Pharmacol Toxicol, 2006, 46:101-122.
Majoosi et al., "Key Attributes of TKDL: Saoot Baraae Sara," Kaamil-al-Sena'ah, Central Council for Research in Unani Medicine, 2005, 2 pages (with English translation).
Malfait et al., "The nonpsychoactive cannabis constituent cannabidiol is an oral anti-arthritic therapeutic in murine collagen-induced arthritis," PNAS, Aug. 15, 2000, 97(17):9561-9566.
Manni et al., "Obstructive Sleep Apnea in a Clinical Series of Adult Epilepsy Patients: Frequency and Features of the Comorbidity," Epilepsia, Jun. 2003, 44(6): 836-840.
Manno, "Status Epilepticus: Current Treatment Strategies," The Neurohospitalist, Jan. 2011, 1(1):23-31.
Mares et al., "Chapter 12: Electrical Stimulation-Induced Models of Seizures," Model of Seizures and Epilepsy, Asla Pitkanen, Philip A. Schwartzkroin & Solomon L. Moshe, eds., 2004, 153-159.
Martin et al., "Structure-Anticonvulsant Activity Relationships of Cannabidiol Analogs," National Institute on Drug Abuse, Research Monograph Series, 1987, 79:48-58.

(56) References Cited

OTHER PUBLICATIONS

Mattson et al., "Comparison of carbamazepine, phenobarbital, phenytoin, and primidone in partial and secondarily generalized tonic-clonic seizures," N Engl J Med, Jul. 18, 1985, 313(3):145-151.
Mattson et al., "Prognosis for total control of complex partial and secondary generalized tonic clonic seizures," Neurology, 1996, 47:68-76.
McCormick et al., "On the Cellular Network Bases of Epileptic Seizures," Annu Rev Physiol, 2001, 63:815-846.
McNamara, "Chapter 19: Pharmacotherapy of the Epilepsies,", Goodman & Gilman's The Pharmacological Basis of Therapeutics 11th ed., McGraw-Hill Companies, 2006, 501-525.
Mechoulam et al., "Cannabidiol: An Overview of Some Pharmacological Aspects," J Clin Pharmacol, 2002, 42:11S-19S.
Mechoulam et al., "Toward drugs derived from cannabis," Naturwissenschaften, Apr. 1978, 65(4): 174-179.
Medicines Q&As: Cannabis-based medicinal products—potential drug interactions, Prepared by UK Medicines Information (UKMi) pharmacists for NHS healthcare professionals, Nov. 29, 2018, 5 pages.
Medicos [online], "Convulsive Disorders and Their Interference with Driving," Medicos, 2014, retrieved Feb. 10, 2017, URL <https://www.medicosporlaseguridadvial.com/en/clinicalsubjects/neurologic-diseases/convulsive-disorders-and-their-interference-with-driving/>, 3 pages.
Merlis, "Proposal for an International Classification of the Epilepsies," Epilepsia, 1970, 11:114-119.
Miller et al., "Mapping genetic modifiers of survival in a mouse model of Dravet syndrome," Genes, Brain and Behavior, 2014, 13:163-172.
Moral et al., "Pipeline on the Move," Drugs of the Future, Jan. 2014, 39(1):49-56.
Morard et al., "Conversion to Sirolimus-Based Immunosuppression in Maintenance Liver Transplantation Patients," Liver Transplantation, 2007, 13:658-664.
MyVirtualMedicalCentre [online], "Aicardi syndrome," mvmc.com, Feb. 2004, retrieved on Jan. 25, 2019, htlPs://www.myvmc.com/diseases/aicardi-syndrome/, 6 pages.
Neto et al., "The role of polar phytocomplexes on anticonvulsant effects of leaf extracts of *Lippia alba* (Mill.) N.E. Brown chemotypes," J. Pharm Pharmacol, 2009, 61(7):933-939.
Ng et al., "Illicit Drug Use and the Risk of New-Onset Seizures," Am J Epidemiol, 1990, 132(1):47-57.
Oakley et al., "Dravet Syndrome Insights into pathophysiology and therapy from a mouse model of Dravet syndrome," Epilepsia, Apr. 2011, 52(Suool. 2):59-61.
Obay et al., "Antiepileptic effects of ghrelin on pentylenetetrazole-induced seizures in rats," Peptides, Jun. 2007, 28(6):1214-1219.
PCT International Preliminary Report on Patentability in International Appln. No. PCT/GB2010/051066, dated Jun. 9, 2011, 6 pages.
PCT International Preliminary Report on Patentability in International Appln. No. PCT/GB2012/052284, dated Dec. 12, 2013, 12 pages.
PCT International Preliminary Report on Patentability in International Appln. No. PCT/GB2015/05177 5, dated Aug. 10, 2016, 9 pages.
PCT International Preliminary Report on Patentability in International Appln. No. PCT/GB2015/053030, dated Apr. 18, 2017, 6 pages.
PCT International Preliminary Report on Patentability in International Appln. No. PCT/GB2016/051792, dated Sep. 1, 2017, 14 pages.
PCT International Preliminary Report on Patentability in International Appln. No. PCT/US2017/050868, dated Oct. 11, 2018, 7 pages.
PCT International Search Report and Written Opinion in International Appln. No. PCT/GB2010/051066 dated Dec. 13, 2010, 8 pages.
PCT International Search Report and Written Opinion in International Appln. No. PCT/GB2011/050649, dated May 30, 2011, 15 pages.
PCT International Search Report and Written Opinion in International Appln. No. PCT/GB2012/052284, dated Nov. 16, 2012, 11 pages.
PCT International Search Report and Written Opinion in International Appln. No. PCT/GB2015/051775, dated Aug. 26, 2015, 11 pages.
PCT International Search Report and Written Opinion in International Appln. No. PCT/GB2015/051776, dated Aug. 25, 2015, 11 pages.
PCT International Search Report and Written Opinion in International Appln. No. PCT/GB2016/052340, dated Oct. 25, 2016, 12 pages.
PCT International Search Report and Written Opinion in International Appln. No. PCT/GB2017/051913, dated Sep. 15, 2017, 9 pages.
PCT International Search Report and Written Opinion in International Appln. No. PCT/GB2017/051914, dated Sep. 12, 2017, 10 pages.
PCT International Search Report and Written Opinion in International Appln. No. PCT/GB2017/053735, dated Mar. 14, 2018, 14 pages.
PCT International Search Report and Written Opinion in International Appln. No. PCT/US2017/050868, dated Aug. 6, 2017, 14 pages.
PCT International Search Report and Written Opinion in International Appln. PCT/GB2017/051943, dated Sep. 12, 2017, 10 pages.
PCT International Search Report in International Appln. No. PCT/GB2012/050002, dated Feb. 24, 2012, 3 pages.
Pelliccia et al. [online], "Treatment with CBD in oily solution of drug-resistant paediatric epilepsies," 2005 Congress on Cannabis and the Cannabinoids, Leiden, The Netherlands: International Association for Cannabis as Medicine, 2005, 14, retrieved on Jun. 30, 2015, URL <http://www.cannabis-med.org/studies/ww_en_db_study_show.php?s_id=I73&&search_pattern=EPILEPSY>, 2 pages, Abstract only.
Pereira et al., "Study pharmacologic of the GABAergic and glutamatergic drugs on seizures and status epilepticus induced by pilocarpine in adult Wistar rats," Neurosci Lett, Jun. 2007, 419(3):253-257.
Pertwee, "Cannabinoid receptor ligands: clinical and neuropharmacological considerations, relevant to future drug discovery and development," Expert Opin Investig Drugs, Jul. 2000, 9(7):1553-1571.
Pertwee, "Chapter 3: The Pharmacology and Therapeutic Potential of Cannabidiol," Cannabinoids, Ed Vincenzo Di Marzo ed., 2004, 32-83.
Pertwee, "The diverse CB1 and CB2 receptor pharmacology of three plant cannabinoids: A9-tetrahydrocannabinol, cannabidiol and A9-tetrahydrocannabivarin," Br. J. Pharmacol, 2008, 153(2):199-215.
Perucca, "Clinically relevant drug interactions with antiepileptic drugs", British Journal of Clinical Pharmacology, 2005, vol. 61, No. 3, p. 246-255.
Perucca, "Pharmacologic Advantages of Antiepileptic Drug Monotherapy", Epilepsia, 1997, vol. 35, No. 5, S6-S8.
Petrocellis et al., "Effects of cannabinoids and cannabinoid-emiched Cannabis extracts on TRP channels and endocannabinoid metabolic enzymes," British Journal of Pharmacology, 2011, 163:1479-1494.
Physician's Desk Reference, 63rd Ed., 2009, 423-431, 2192-2194, 2639-2242, 3019-3022.
Pisani, "Influence of co-medication on the metabolism of valproate", Pharmaceutish Weekblad Scientific Edition, 1992, vol. 14, No. 3A, p. 108-113.
Pohl et al., "Effects of flunarizine on Metrazol-induced seizures in developing rats," Epilepsy Res, 1987, 1:302-305.
Poortman—van der Meer, "A contribution to the improvement of accuracy in the quantitation of THC," Forensic Science International, Apr. 1999, 101(1):1-8.

(56) References Cited

OTHER PUBLICATIONS

Porter et al., "Randomized, multicenter, dose-ranging trial of retigabine for partial-onset seizures," Neurology, Apr. 2007, 68(15):1197-1204.
Porter et al., "Report of a Parent Survey of Cannabidiol-emiched Cannabis use in Pediatric Treatment-resistant Epilepsy," Epilepsy Behavior, Dec. 2013, 29(3):574-577.
Potter, "Chapter 4: Cannabis Horticulture," Handbook of Cannabis, ed. Roger G. Pertwee, 2014, 65-88.
Pouton, "Lipid formulations for oral administration of drugs: non-emulsifying, self- emulsifying and 'self-microemulsifying' drug delivery systems, "Eur. J Phann Sci, Oct. 2000, 1I(Supp. 2):S93-S98.
Press et al., "Parental reporting of response to oral cannabis extracts for treatment of refractory epilepsy," Epilepsy Behav, Apr. 2015, 45:49-52.
Pruitt et al., "Ethanol in Liquid Preparations Intended for Children," Padiatrics, Mar. 1984: 73(3):405-407.
Rabinski [online], "CBD-A: Cannabidiol Acid Cannabinoid Profile," MassRoots, Jul. 2, 2015, retrieved on Jan. 31, 2018, URL <https://www.massroots.com/learn/can-the-cbd-a-cannabinoid- help-you/>, 4 pages.
Ramantani et al., "Epilepsy in Aicardi—Goutieres syndrome," Official J Eur Paediatric Neurology Society, 2014, 18:30-37.
Rauca et al., "The role of superoxide dismutase and a-tocopherol in the development of seizures and kindling induced by pentylenetetrazol—influence of the radical scavenger a-phenyl-N-tert-butyl nitrone," Brain Research, May 29, 2004, 1009(1-2):203-212.
Resstel et al., "5-HTIA receptors are involved in the cannabidiol-induced attenuation of behavioural and cardiovascular responses to acute restraint stress in rats," Br J Pharmacol, Jan. 2009, 156(1):181-188.
Rosenberg et al., "Cannabinoids and Epilepsy," Neurotherapeutics, Oct. 2015, 12(4):747-768.
Rosenkrantz et al., "Oral and Parenteral Formulations of Marijuana Constituents," J Phann Sci, Jul. 1972, 61(7)1106-1112.
Rubio et al., "In Vivo Experimental Models of Epilepsy," Central Nervous System Agents in Medicinal Chemistry, 2010, 10:298-309.
Russo, "Taming THC: potential cannabis synergy and phytocannabinoid-terpenoid entourage effects, " British J. of Phann, 2011, 163:1344-1364.
Sadanandasarma et al., "Key Attributes of TKDL: Suddha Bhanga Visista Gunah Aur Matra," Rasatarangini 11th Ed., 1979:720-723 (with English translation).
SalutarisDrops.com [online], "Cannabidiol for Aicardi Syndrome," Salutaris, available on or before Oct. 2014, retrieved on Feb. 10, 2017, URL <http://web.archive.org/web/20141012220050/http://salutarisdrops.com/cannabidiol-aicardi-syndrome/>, 3 pages.
Sander, "The epidemiology of epilepsy revisited," Curr Opin Neurol, Apr. 2003, 16(2):165-170.
Sandyk et al., "Preliminary trial of cannabidiol in Huntington's Disease," Marihuana: An International Research Report, 1988, 157-162.
Sastri et al., "Key Attributes of TKDL: Vijaya Kalpah (Apasmaranasaka)," Anandakandam 1st ed., 1952:241, 5 pages (with English translation).
Scuderi et al., "Cannabidiol in Medicine: A Review of its Therapeutic Potential in CNS Disorders," Phytother Res, May 2009, 23(5):597-602.
Shukla [online], "New Automated Purification Strategies for Scale-Up," PCISyntesis.com, posted Dec. 25, 2017, https://www.pcisynthesis.com/new-automated-purification-strategies-for-scale-up/, 5 pages.
Silva et al., "Clobazam as Add-on Therapy in Children with Epileptic Encephalopathy," Can J Neurol Sci, 2006 33:209-213.
Sperling et al., "Carisbamate as adjunctive treatment of partial onset seizures in adults in two randomized, placebo-controlled trials," Epilepsia, Mar. 2010, 51(3):333-343.
Stafstrom et al., "Models of Pediatric Epilepsies: Strategies and Opportunities," Epilepsia, 2006, 47(8):1407-1414.
Stephenson, "In Memoriam: Professor Jean Aicardi (1926-2015)," Pediatric Neurology, Jan. 2016, 54:3-4.
Stott et al., "Cannabinoids for the pharmaceutical industry," Euphytica, 2004, 140:83-93.
Strickley, "Solubilizing Excipients in Oral and Injectable Formulations," Table VIII, Pharmaceutical Research, Feb. 2004, 21(2):201-230.
Swann, "The Effects of Seizures on the Connectivity and Circuitry of the Developing Brain," MRDD, 2004, 10(2):96-100.
Thomas et al., "Cannabidiol displays unexpectedly high potency as an antagonist of CB1 and CB2 receptor agonists in vitro," British J Pharmacology, 2007, 150(5):613-623.
Thomas et al., "Evidence that the Plant Cannabinoid /19-Tetrahydrocannabivarin is a Cannabinoid CBI and CB2 Receptor antagonist," Br J Pharmacol, Dec. 2005, 146(7):917-926.
Thumma et al., "Influence of plasticizers on the stability and release of a prodrug of !!,,9-tetrahydrocannabinol incorporated in poly (ethylene oxide) matrices," Eur J Pharmceutics and Biopharmaceutics, Oct. 2008, 70(2):605-614.
Thurman et al., "Standards for epidemiologic studies and surveillance of epilepsy," Epilepsia, Sep. 2011, 52 Suool 7:2-26.
Thurstone, "Avoid Charlotte's Web for Epilepsy," Jun. 26, 2014, URL <http://drthurstone.com/charlotted-web-not-safest-option-epilepsy-treatment/>, 4 pages.
Trembly and Sherman, "Double-blind clinical study of cannabidiol as a secondary anticonvulsant," Marijuana '90 Int. Conf. on Cannabis and Cannabinoids, Kolympari (Crete), Jul. 8-11, 1990, 1 page, Abstract Only.
Turkanis et al., "An Electrophysiological Analysis of the Anticonvulsant Action of Cannabidiol on Limbic Seizures in Conscious Rats," Epilepsia, 1979, 20:351-363.
U.S. Department of Health and Human Services, Food and Drug Administration Center for Drug Evaluation and Research (CDER), "Guidance for Industry Estimating the Maximum Safe Starting Dose in Initial Clinical Trials for Therapeutics in Adult Healthy Volunteers," Jul. 2005, 30 pages.
Unimed Pharmaceuticals, Inc., "Marino!®," Jul. 2006 <https://www.accessdata.fda.gov/drugsatfda docs/label/2006/018651s025s026lbl.pdt>, 11 pages.
Usami et al., "Synthesis and Pharmacological Evaluation in Mice of Halogenated Cannabidiol Derivatives," Chem Pharm Bull, Nov. 1999, 47(11):1641-1645.
USPTO Information Disclosure Statement Form PTO-1449 in U.S. Appl. No. 13/380,305, dated Nov. 24, 2014, 8 pages.
USPTO Notice of Allowance in U.S. Appl. No. 13/380,305, dated Dec. 10, 2014, 5 pages.
USPTO Notice of Allowance in U.S. Appl. No. 13/380,305, dated Mar. 19, 2015, 7 pages.
USPTO Office Action in U.S. Appl. No. 13/380,305, dated Aug. 25, 2014, 6 pages.
USPTO Request for Continued Examination with the Amendment and Information Disclosure Statement in U.S. Appl. No. 13/380,305, filed Mar. 2, 2015, 8 pages.
USPTO Third Preliminary Amendment under 37 C.F.R. 1.115 in U.S. Appl. No. 13/380,305, dated May 23, 2014, 4 pages.
Utah.gov [online], "2nd Agenda Controlled Substances Advisory Committee Meeting," Nov. 12, 2013, URL <https://www.utah.gov/pmn/files/81459.pdf>, 63 pages.
Van Rijckevorsel, "Treatment of Lennox-Gastaut Syndrome: overview and recent fmdings," Neuropsychiatr Dis Treat, Dec. 2008, 4(6):1001-1019.
Velisek, "Chapter 11: Models of Chemically-Induced Acute Seizures," Models of Seizures and Epilepsy, 2006, 127-152.
Veliskova, "Chapter 48: Behavioral Characterization of Seizures in Rats," Models Seizures Epilepsy, 2006, 601-611.
Vietnam Office Action in Application No. 1201400886, dated Sep. 24, 2019, 2 pages, English Translation.
Vollner et al., "Haschisch XX+ [Haschiscc XX+]: Cannabidivarin, a new hashish substance," Tetrahedron Letters, 1969, 10(3):145-147.
Wallace et al., "Assessment of the role of CBI receptors in cannabinoid anticonvulsant effects," European J Pharmacology, 2001, 428(1):51-57.

(56) References Cited

OTHER PUBLICATIONS

Wallace et al., "Pharmacotherapy for Dravet syndrome," Pediatr. Drugs, Jun. 2016, 18:197-208.
Weston et al., "Tetrahydrocannabivarin Exhibits Anticonvulsant Effects in a Piriform Cortical Brain Slice Model ofEpileptiform Activity," Proceedings of the British Phann Society, Dec. 2006, retrieved on Mar. 1, 2017, URL <http://www.pA2online.org/abstract/abstract.jsp?abid=28533>, 1 page, Abstract Only.
Wikipedia.org [online], "Cannabinoid," Wikipedia, Apr. 2003, retrieved on Mar. 1, 2017, URL <https://en.wikipedia.org/wiki/Cannabinoid>, 15 pages.
Wingerchuk, "Cannabis for medical purposes: cultivating science, weeding out the fiction," Lancent, Jul. 2004, 364:315-316.
Yu et al., "Reduced sodium current in GABAergic intemeurons in a mouse model of severe myoclonic epilepsy in infancy," Nature Neuroscience, Sep. 2006, 9(9):1142-1149.
Yuriev, "Endogenic Cannabinoid System is a New Perspective Object of Pharmacotherapeutic Effect to Disease of Nervous System," Ukrainsky Metodichny Chasopis, 2005, 6(50):21-29 (with English Abstract).
Zamberletti et al., "Alterations of prefrontal cortex GABAergic transmission in the complex psychotic-like phenotype induced by adolescent delta-9-tetrahydrocannabinol exposure in rats," Neurobiology of Disease, Mar. 2014, 63:35-47.
Zhao et al., "Chapter 27: Repetitive Seizures in the Immature Brain," Models of Seizures and Epilepsy, 2006, 341-350.
Zhomitsky and Potvin, "Cannabidiol in Humans—The Quest for Therapeutic Targets," Pharmaceuticals, 2012, 5:529-552.
Zuardi et al., "Cannabidiol, a Cannabis sativa constituent, as an antipsychotic drug," Brazilian Journal of Medicine and Biological Research, Apr. 2006, 39(4):421-429.
Zuardi et al., "Cannabidiol: from an inactive cannabinoid to a drug with wide spectrum of action," Rev Bras Psiquiatr, 2008, 30(3):271-80.
U.S. Appl. No. 15/640,033, filed Jun. 30, 2017; Inventor(s): Jitinder Wilkhu et al.
U.S. Appl. No. 16/768,241, filed May 29, 2020; Inventor(s): Geoffrey Guy et al.
U.S. Appl. No. 16/959,354, filed Jun. 30, 2020; Inventor(s): Jitinder Wilkhu et al.
U.S. Appl. No. 16/935,005, filed Jul. 21, 2020; Inventor(s): Geoffrey Guy et al.
U.S. Appl. No. 17/012,448, filed Sep. 4, 2020; Inventor(s): Benjamin Whalley et al.
U.S. Appl. No. 17/050,956, filed Oct. 27, 2020; Inventor(s): Geoffrey Guy et al.
U.S. Appl. No. 17/102,109, filed Nov. 23, 2020; Inventor(s): Guillermo Velasco Diez et al.
U.S. Appl. No. 17/231,625, filed Apr. 15, 2021; Inventor(s): Stephen Wright et al.
U.S. Appl. No. 17/296,066, filed May 21, 2021; Inventor(s): Geoffrey Guy et al.
U.S. Appl. No. 17/296,076, filed May 21, 2021; Inventor(s): Geoffrey Guy et al.
U.S. Appl. No. 17/424,682, filed Jul. 21, 2021; Inventor(s): Geoffrey Guy et al.
U.S. Appl. No. 17/426,442, filed Jul. 28, 2021; Inventor(s): Geoffrey Guy et al.
U.S. Appl. No. 17/406,401, filed Aug. 19, 2021; Inventor(s): Jitinder Wilkhu et al.
U.S. Appl. No. 17/435,892, filed Sep. 2, 2021; Inventor(s): Geoffrey Guy et al.
U.S. Appl. No. 17/606,370, filed Oct. 25, 2021; Inventor(s): Geoffrey Guy et al.
U.S. Appl. No. 17/611,824, filed Nov. 16, 2021; Inventor(s): Geoffrey Guy et al.
U.S. Appl. No. 17/548,232, filed Dec. 10, 2021; Inventor(s): Stephen Wright et al.
U.S. Appl. No. 17/627,946, filed Jan. 18, 2022; Inventor(s): Alan James Silcock et al.
U.S. Appl. No. 17/585,415, filed Jan. 26, 2022; Inventor(s): Benjamin Whalley et al.
U.S. Appl. No. 17/631,069, filed Jan. 28, 2022; Inventor(s): Geoffrey Guy et al.
U.S. Appl. No. 17/638,629, filed Feb. 25, 2022; Inventor(s): Benjamin Whalley et al.
U.S. Appl. No. 17/689,607, filed Mar. 8, 2022; Inventor(s): Geoffrey Guy et al.
U.S. Appl. No. 17/689,245, filed Mar. 8, 2022; Inventor(s): Harshit Shah.
U.S. Appl. No. 17/768,048, filed Apr. 11, 2022; Inventor(s): Geoffrey Guy et al.
U.S. Appl. No. 17/770,435, filed Apr. 20, 2022; Inventor(s): Geoffrey Guy et al.
U.S. Appl. No. 17/770,436, filed Apr. 20, 2022; Inventor(s): Geoffrey Guy et al.
U.S. Appl. No. 17/771,184, filed Apr. 22, 2022; Inventor(s): Geoffrey Guy et al.
U.S. Appl. No. 17/771,190, filed Apr. 22, 2022; Inventor(s): Geoffrey Guy et al.
U.S. Appl. No. 17/771,195, filed Apr. 22, 2022; Inventor(s): Geoffrey Guy et al.
U.S. Appl. No. 17/771,183, filed Apr. 22, 2022; Inventor(s): Geoffrey Guy et al.
U.S. Appl. No. 17/744,224, filed May 13, 2022; Inventor(s): Geoffrey Guy et al.
U.S. Appl. No. 17/777,734, filed May 18, 2022; Inventor(s): Geoffrey Guy et al.
U.S. Appl. No. 17/777,677, filed May 18, 2022; Inventor(s): Geoffrey Guy et al.
U.S. Appl. No. 17/777,681, filed May 18, 2022; Inventor(s): Geoffrey Guy et al.
U.S. Appl. No. 17/841,167, filed Jun. 15, 2022; Inventor(s): Geoffrey Guy et al.
U.S. Appl. No. 17/786,949, filed Jun. 17, 2022; Inventor(s): Alan James Silcock et al.
U.S. Appl. No. 17/853,367, filed Jun. 29, 2022; Inventor(s): Geoffrey Guy et al.
U.S. Appl. No. 17/817,753, filed Aug. 5, 2022; Inventor(s): Volker Knappertz et al.
U.S. Appl. No. 18/002,437, filed Dec. 19, 2022; Inventor(s): Jie Li et al.
U.S. Appl. No. 18/005,838, filed Jan. 17, 2023; Inventor(s): Daniel Adam Checketts et al.
U.S. Appl. No. 18/005,841, filed Jan. 17, 2023; Inventor(s): Daniel Adam Checketts et al.
U.S. Appl. No. 18/005,843, filed Jan. 17, 2023; Inventor(s): Daniel Adam Checketts et al.
U.S. Appl. No. 18/005,845, filed Jan. 17, 2023; Inventor(s): Daniel Adam Checketts et al.
U.S. Appl. No. 18/005,847, filed Jan. 17, 2023; Inventor(s): Daniel Adam Checketts et al.
U.S. Appl. No. 18/005,848, filed Jan. 17, 2023; Inventor(s): Daniel Adam Checketts et al.
U.S. Appl. No. 18/005,851, filed Jan. 18, 2023; Inventor(s): Daniel Adam Checketts et al.
U.S. Appl. No. 18/005,852, filed Jan. 18, 2023; Inventor(s): Daniel Adam Checketts et al.
U.S. Appl. No. 18/005,853, filed Jan. 18, 2023; Inventor(s): Daniel Adam Checketts et al.
U.S. Appl. No. 18/005,868, filed Jan. 18, 2023; Inventor(s): Daniel Adam Checketts et al.
U.S. Appl. No. 18/005,959, filed Jan. 18, 2023; Inventor(s): Daniel Adam Checketts et al.
U.S. Appl. No. 18/005,960, filed Jan. 18, 2023; Inventor(s): Daniel Adam Checketts et al.
U.S. Appl. No. 18/005,961, filed Jan. 18, 2023; Inventor(s): Daniel Adam Checketts et al.
U.S. Appl. No. 18/006,121, filed Jan. 19, 2023; Inventor(s): Daniel Adam Checketts et al.
U.S. Appl. No. 18/006,125, filed Jan. 19, 2023; Inventor(s): Daniel Adam Checketts et al.

(56) References Cited

OTHER PUBLICATIONS

U.S. Appl. No. 18/006,127, filed Jan. 19, 2023; Inventor(s): Daniel Adam Checketts et al.
U.S. Appl. No. 18/006,129, filed Jan. 19, 2023; Inventor(s): Daniel Adam Checketts et al.
U.S. Appl. No. 18/006,131, filed Jan. 19, 2023; Inventor(s): Daniel Adam Checketts et al.
U.S. Appl. No. 18/006,133, filed Jan. 19, 2023; Inventor(s): Daniel Adam Checketts et al.
U.S. Appl. No. 18/161,603, filed Jan. 30, 2023; Inventor(s): William Hind et al.
U.S. Appl. No. 18/170,235, filed Feb. 16, 2023; Inventor(s): Geoffrey Guy et al.
U.S. Appl. No. 18/043,810, filed Mar. 2, 2023; Inventor(s): Michael Simon Loft et al.
U.S. Appl. No. 18/044,941, filed Mar. 10, 2023; Inventor(s): Kevin James Craig et al.
U.S. Appl. No. 18/245,856, filed Mar. 17, 2023; Inventor(s): Kevin James Craig et al.
U.S. Appl. No. 18/186,792, filed Mar. 20, 2023; Inventor(s): Geoffrey Guy et al.
U.S. Appl. No. 18/311,221, filed May 2, 2023; Inventor(s): Geoffrey Guy et al.
U.S. Appl. No. 18/256,307, filed Jun. 7, 2023; Inventor(s): Daniel Adam Checketts et al.
U.S. Appl. No. 18/257,373, filed Jun. 14, 2023; Inventor(s): Alan James Silcock et al.
U.S. Appl. No. 18/257,537, filed Jun. 14, 2023; Inventor(s): Alan James Silcock et al.
U.S. Appl. No. 18/257,479, filed Jun. 14, 2023; Inventor(s): Karen Ka-Yen Tse et al.
U.S. Appl. No. 18/258,485, filed Jun. 20, 2023; Inventor(s): Kevin James Craig et al.
U.S. Appl. No. 18/446,405, filed Aug. 8, 2023; Inventor(s): Geoffrey Guy et al.
U.S. Appl. No. 18/546,254, filed Aug. 11, 2023; Inventor(s): Karen Ka-Yen Tse.
U.S. Appl. No. 18/548,003, filed Aug. 25, 2023; Inventor(s): Volker Knappertz et al.
U.S. Appl. No. 18/477,467, filed Sep. 28, 2023; Inventor(s): Jitinder Wilkhu et al.
U.S. Appl. No. 18/479,671, filed Oct. 2, 2023; Inventor(s): Alan James Silcock et al.
U.S. Appl. No. 18/560,316, filed Nov. 10, 2023; Inventor(s): Alan James Silcock et al.
U.S. Appl. No. 18/560,337, filed Nov. 10, 2023; Inventor(s): Alan James Silcock et al.
U.S. Appl. No. 18/560,341, filed Nov. 10, 2023; Inventor(s): Alan James Silcock et al.
U.S. Appl. No. 18/560,346, filed Nov. 10, 2023; Inventor(s): Alan James Silcock et al.
U.S. Appl. No. 18/526,795, filed Dec. 1, 2023; Inventor(s): Geoffrey Guy et al.
U.S. Appl. No. 18/545,754, filed Dec. 19, 2023; Inventor(s): Geoffrey Guy et al.
U.S. Appl. No. 18/292,844, filed Jan. 26, 2024; Inventor(s): Volker Knappertz.
U.S. Appl. No. 18/597,717, filed Mar. 6, 2024; Inventor(s): Jonathan Oliver Whitehouse et al.
Combined Search and Exam Report dated Apr. 24, 2017 for GB Application No. GB1614522.9, 4 pages.
Combined Search and Exam Report dated Dec. 8, 2017 for GB Application No. GB1703115.4 5 pages.
Combined Search and Exam Report dated Jul. 6, 2021 for GB Application No. GB2102010.2, 4 pages.
Combined Search and Examination Report mailed Feb. 27, 2018 for GB Application No. GB1410771.8, 7 pages.
Combined Search and Examination Report mailed Feb. 25, 2016 for GB Application No. GB1510664.4, 6 pages.
Communication Pursuant to Article 94(3) EPC in European Patent Application No. GB10734541.5, dated Oct. 23, 2012, 3 pages.
Declaration of Sean D. McAllister and Pierre-Yves Desprez dated Nov. 26, 2012, filed in U.S. Appl. No. 12/600,553, 19 pages.
Notice of Opposition to European Patent No. EP2448637, dated Dec. 5, 2014, 20 pages.
Opponent's Response to the Written Submissions in European Patent No. EP2448637, dated Oct. 20, 2016, 3 pages.
Opponent's Written Submission in European Patent No. EP2448637, dated Nov. 4, 2016, 3 pages.
Patentee's Response and Amended Claim Set for EP09757810.8, dated Sep. 27, 2013, 9 pages.
PCT International Search Report and Written Opinion mailed Apr. 20, 2018 for International Application No. PCT/GB2018/050421, 12 pages.
PCT International Search Report and Written Opinion mailed Oct. 6, 2017 for International Application No. PCT/GB2017/052229, 10 pages.
PCT International Search Report and Written Opinion mailed Feb. 5, 2016 in International Application No. PCT/GB2015/053028, 13 pages.
PCT Written Opinion for International Application No. PCT/GB2010/051066, dated Nov. 16, 2010, 4 pages.
PCT International Search Report and Written Opinion mailed May 2, 2022 for International Application No. PCT/GB2022/050221, 8 pages.
PCT International Search Report and Written Opinion mailed Aug. 31, 2016 in International Application No. PCT/GB/2016/051792, 13 pages.
PCT International Preliminary Report on Patentability in International Appl. No. PCT/GB2017/052229, dated Feb. 26, 2019, 7 pages.
PCT International Search Report and Written Opinion in International Application No. PCT/GB2015/053024, dated Feb. 2, 2016, 9 pages.
PCT International Search Report and Written Opinion for International Application No. PCT/GB2010/0051066, mailed Dec. 13, 2010, 8 pages.
PCT International Preliminary Report on Patentability mailed Oct. 4, 2006 for PCT Application No. PCT/GB2005/003793, filed on Sep. 30, 2005, 6 pages.
PCT International Preliminary Report on Patentability mailed Sep. 18, 2012 for PCT Application No. PCT/GB2011/050478, 6 pages.
PCT International Search Report and Written Opinion mailed Jan. 16, 2006 for PCT Application No. PCT/GB2005/003793, 10 pages.
PCT International Search Report and Written Opinion mailed Aug. 2, 2011 for PCT Application No. PCT/GB2011/050487, 22 pages.
Reply to EPO Communication in European Patent No. EP2448637, dated Nov. 2, 2016, 45 pages.
Reply to Preliminary Opinion and Opponent's Observations in European Patent No. EP2448637, dated Sep. 15, 2016, 65 pages.
Statement of Opposition for EP2448637, mailed Dec. 5, 2014, 14 pages.
USPTO Decision on Appeal in U.S. Appl. No. 10/318,659 (Appeal 2009-011751), dated Jul. 8, 2010, 23 pages.
USPTO Decision on Appeal in U.S. Appl. No. 13/698,730 (Appeal 2016-006258), dated Jun. 21, 2017, 6 pages.
[Author Unknown], Drug Development & Delivery (2018). "GW Pharmaceuticals Achieves Positive Results in Phase II Study," available online at <https://drug-dev.com/gw-pharmaceuticals-achieves-positive-results-in-phase-ii-study/, 4 pages.
[Author Unknown], "Lennox-Gastaut Syndrome," Child Neurology Foundation, available on or before Sep. 6, 2005, retrieved on May 21, 2018, <http://childneurologyfoundation.org/disorders/lgs-lennox-gasaut-syndrome>, 10 pages.
[Author Unknown], Models of Chemically-Induced Acute Seizures, Models of Seizures and Epilepsy, Elsevier, 2006, p. 127.
[Author Unknown] Salutaris Drops Buy Salutaris Drops—Salutaris Drops. Oct. 12, 2014. Last accessed on Jan. 20, 2017 at http:/web.archive.org/web/20141012130255/http://salutarisdrops.com/buy-salutaris-drops, 2 pages.
[Author Unknown] Salutaris Drops Cannabidiol for Aicardi Syndrome—Salutaris Drops, Oct. 12, 2014. Last accessed from http://web.

(56) References Cited

OTHER PUBLICATIONS archive.org/web/20141012220050/http://salutarisdrops.com/cannabidiol-aicardi-syndrome/ on Apr. 20, 2021, 3 pages.
[Author Unknown] Database WPI Week 201252. Clarivate Analytics, Accession No. 2012-J67237, Jan. 8, 2011, 2 pages.
[Author Unknown] GWPharm [online], "GW Pharmaceuticals Announces Preliminary Results of Phase 2a Study for its Pipeline Compound GWP42006," GW Pharmaceuticals Press Release, Feb. 21, 2018, https://www.globenewswire.com/news-release/2018/02/21/1372900/0/en/GW-Pharmaceuticals-Announces-Preliminary-Results-of-Phase-2a-Study-for-its-Pipeline-Compound-GWP42006.html, 5 pages.
[Author Unknown] American Association of Neurological Surgeons (AANS), "Glioblastoma Multiforme," Mar. 2015, last updated Mar. 2015; https://www.aans.org/, 5 pages.
Adalpe et al., "Models of malignant glioma," Drug Discovery Today: Disease Models, 3(2):191-196 (2006).
Arrieta et al., "Protamine inhibits angiogenesis and growth of C6 rat glioma; a synergistic effect when combined with carmustine," Ep J. of Cancer, 34(13):2101-2106 (1998).
Ben-Shabat, et al., "New cannabidiol derivatives: synthesis, binding to cannabinoid receptor, and evaluation of their ant-inflammatory activity," J Med Chem., 49(3):1113-1117 (2006).
Berk et al., "Investigating owner use of dietary supplements in dogs with idiopathic epilepsy," Res Vet Sci, 119:276-284 (2018). doi: 10.1016/j.rvsc.2018.07.004. Epub Jul. 24, 2018.
Berrocal, et al., "Temozolamide in previously treated high-grade gliomas patients," J. of Cancer, 37:S343 (2001). Poster 1275, presented on Oct. 24, 2001, 1 page.
Bialer et al., "Progress report on new antiepileptic drugs: a summary of the fourth Eilat conference (Eilat IV)," Epilepsy Research, 111:85-141 (2015).
Blazquez, et al., "Inhibition of tumor angiogenesis by cannabinoids," FASEB J, 17:529-531 (2003).
Blow, "Cell migration: our protruding knowledge," Nature Methods., 4(7):589-594 (2007).
Boiardi, et al., "Efficacy of '8-drugs-in-one-day' combination in treatment of recurrent GBM patients," Journal of Neuro-Oncology, 12:153-158 (1992).
Boyden, "The chemotactic effect of mixtures of antibody and antigen on polymorphonuclear leucocytes," J Exp Med, 115:453-456 (1962).
Casanova et al., "Inhibition of skin tumor growth and angiogenesis in vivo by activation of cannabinoid receptors," J. Clinical Investigation, 111(1):43-50 (2003).
cdc.gov [online]. "2 to 20 years: girls Stature-for-age and Weigh-for-age percentiles," National Center for Health Statistics and National Center for Chronic Disease Prevention and Health Promotion, last modified Nov. 2000, <https://www.cdc.gov/growthcharts/data/set1clinical/cj4aa022.pdf>, 1 page.
Chang et al., "Signal transduction mediated by the Ras/Raf/MEK/ERK pathway from cytokine receptors to transcription factors: potential targeting for therapeutic intervention," Leukemia, 7(7):1263-1293 (2003).
Chou, "Theoretical basis, experimental design, and computerized simulation of synergism and antagonism in drug combination studies," Pharmacol Rev., 58(3):621-681 (2006).
Chou & Talalay, "Analysis of combined drug effects: a new look at a very old problem," TIPS, 4:450-454 (1983).
Dasa, et al. "Brhat Nighantu Ratnakara (Saligramanighantubhusanam)." vol. IV. 1997:170. Sanskrit. Exhibit 5, 5 pages.
De La Ossa et al., "Local delivery of cannabinoid-loaded microparticles inhibits tumor growth in a murine xenograft model of glioblastoma multiforme," PLoS One, 8(1): e54795 (2013); doi: 10.1371/journal.pone.0054795. Epub Jan. 22, 2013, 8 pages.
De Meijer et al., "The inheritance of chemical phenotype in cannabis sativa L. (II): Cannabigerol predominant plants," Euphytica, 145(1):189-198 (2007).
De Petrocellis et al., "Regulation of transient receptor potential channels of melastatin type 8 (TRPM8): Effect of cAMP, cannabinoid CB1 receptors and endovanilloids," Exp Cell Res., 313(9):1911-1920 (2007). Epub Jan. 18, 2007.
Elsohly and Gul, "Constituents of Cannabis Sativa," Chapter 1, Handbook of Cannabis, Roger G. Pertwee, Ed., pp. 3-22 (2014).
EPIDIOLEX® (cannabidiol) oral solution, CV, Prescribing Information, 2018, 30 pages; https://www.accessdata.fda.gov/drugsatfda_docs/label/2018/210365lbl.pdf.
Fariello, "Parenteral Penicillin in Rats: An Experimental Model of Multifocal Epilepsy," Epilepsia, 17:217-222 (1976).
FDA [Online], "Warning Letters and Test Results for Cannabidiol-Related Products," 2016 Warning Letters, retrieved on Nov. 14, 2017, URL <https://www.fda.gov/newsevents/publichealthfocus/ucm484109.htm, 4 pages.
Fernandes et al., "Modification of delta9-THC-actions by cannabinol and cannabidiol in the rat," Psychopharmacologia, 38(4):329-338 (1974); doi: 10.1007/BF00429130.
Galve-Roperh et al., "Anti-tumoral action of cannabinoids: involvement of sustained ceramide accumulation and extracellular signal-regulated kinase activation," Nature Medicine, 6(3):313-319 (2000).
Gilbert, et al., "A phase II study of temozolomide in patients with newly diagnosed supratentorial malignant glioma before radiation therapy," Neuro-Oncology, 4(4):261-267 (2002).
Grotenhermen, "Pharmacokinetics and Pharmacodynamics of Cannabinoids," Clin. Pharmacokinet., 42(4):327-360 (2003).
Guzman et al., "Control of the cell survival/death decision by cannabinoids," J. Mol Med (Berl)., 78(11):613-625 (2001).
Guzman et al., "Cannabinoids: potential anticancer agents," Nat Rev Cancer, 3(10):745-755 (2003).
Hayakawa et al., "Cannabidiol potentiates pharmacological effects of Delta(9)-tetrahydrocannabinol via CB(1) receptor-dependent mechanism," Brain Res., 1188:157-164 (2003).
Heske et al., "A cohort study of epilepsy among 665,000 insured dogs: Incidence, mortality and survival after diagnosis," The Veterinary Journal, 471-6 (2014); doi:10.1016/j.tvjl.2014.09.023, 6 pages.
Huang et al., "ECRG2 inhibits cancer cell migration, invasion and metastasis through the down-regulation of uPA/plasmin activity," Carcinogenesis, 28(11):2274-2281 (2007); doi: 10.1093/carcin/bgm140/.
Huizenga et al., "Preclinical safety and efficacy of cannabidivarin for early life seizures," Neuropharmacology, 148:189-198 (2019).
Hulkower & Herber, "Cell Migration and Invasion Assays as Tools for Drug Discovery," Pharmaceutics, 3:107-124 (2011).
Izzo et al., "Increased endocannabinoid levels reduce the development of precancerous lesions in the mouse colon," J. Mol Med (Berl.), 86(1):89-98 (2008).
Jacobsson et al., "Serum-dependent effects of tamoxifen and cannabinoids upon C6 glioma cell viability," Biochem Pharmacol, 60(12):1807-1813 (2000).
Jacobsson et al., "Inhibition of rat C6 glioma cell proliferation by endogenous and synthetic cannabinoids. Relative involvement of cannabinoid and vanilloid receptors," J. Pharmacology and Expt. Therapeutics, 299(3):951-959 (2001).
Jones et al., "Cannabinoid receptor systems: therapeutic targets for tumour intervention," Expert Opin Ther Targets, 7(6):749-758 (2003).
Kampa-Schittenhelm et al., Abstract. "Epigenetic hypomethylation of the 5'UTR of NADPH oxidase 4 (NOX4) by cannabidiol (CBD) results in increased protein expression, catalyzation of reactive oxygen species (ROS) and induction of apoptosisin acute leukemia," Oncol. Res. Treat., 40(Suppl 3):22 (2017), 1 page.
Killestein et al., "Safety, tolerability, and efficacy of orally administered cannabinoids in MS," Neurology, 58(9):1404-1407 (2002).
Kramer, et al., "Febrile infection-related epilepsy syndrome (FIRES): pathogenesis, treatment, and outcome: a multicenter study on 77 children," Epilepsia, 52(11):1956-65 (2011); doi:10.1111/j.1528-1167.2011.03250.x. Epub Aug. 29, 2011.
Krajci et al., "Ultrastructure of nuclei of cisplatin-treated C6 glioma cells undergoing apoptosis," EP J. of Cell Biology, 79(5):365-376 (2000).
Kuhn et al., "Potent activity of carfilzomib, a novel, irreversible inhibitor of the ubiquitin-proteasome pathway, against preclinical models of multiple myeloma," Blood, 110(9):3281-3290 (2007).

(56) References Cited

OTHER PUBLICATIONS

Lee et al., "Distinct Topographical Patterns of Spike-Wave Discharge in Transgenic and Pharmacologically Induced Absence Seizure Models," Exp Neurobiol, 28(4):474-484 (2019). doi: 10.5607/en.2019.28.4.474.
Levy et al., "Modulation of the metastatic frequency of a murine mammary adenocarcinoma by a synthetic cannabinoid drug," Seventh Annual Meeting of the American Association for Cancer Research, May 16-19, 1979, AACR Abstract, 2 pages.
Ligresti et al., "Antitumor activity of plant cannabinoids with emphasis on the effect of cannabidiol on human breast carcinoma," J Pharmacol Exp Ther., 318(3):1375-1387 (2006). Epub May 25, 2006.
Liu et al., "Enhancing the in vitro cytotoxic activity of Delta9-tetrahydrocannabinol in leukemic cells through a combinatorial approach," Leuk Lymphoma, 49(9):1800-1809 (2008).
Lopez-Valero et al., "Targeting Glioma Initiating Cells with a combined therapy of cannabinoids and temozolomide," Biochemical Pharmacology, 157:266-274 (2018).
Massi et al., "Antitumour effects of cannabidiol, a nonpsychoactive cannabinoid, on human glioma cell lines," J Pharmacol Exp Ther., 308(3):838-845 (2004). Epub Nov. 14, 2003.
McAllister et al., "Cannabidiol as a novel inhibitor of Id-1 gene expression in aggressive breast cancer cells," Mol Cancer Ther., 6(11):2921-2927 (2007).
McAllister et al., "Molecular Mechanisms of Cannabinoid Antitumor Activity," Research Grant proposal to Forbes Norris/MDA ALS Research Center, submitted as Exhibit A to Declaration by Sean D. McAllister and Pierre-Yves Desprez dated Nov. 26, 2012, filed in U.S. Appl. No. 12/600,553, 15 pages.
McAllister, Excel data reporting results of experiments for "Molecular Mechanisms of Cannabinoid Antitumor Activity," Research Grant Proposal to Forbes orris/MDA ALS Research Center, submitted as Exhibit B to Declaration by Sean D. McAllister and Pierre-Yves Desprez dated Nov. 26, 2012, filed in U.S. Appl. No. 12/600,553, 1 page.
McGrath et al., "Randomized blinded controlled clinical trial to assess the effect of oral cannabidiol administration in addition to conventional antiepileptic treatment on seizure frequency in dogs with intractable idiopathic epilepsy," J Am Vet Med Assoc, 254(11):1301-1308 (2019).
Mechoulam, et al., "Cannabidiol: An Overview of Some Pharmacological Aspects," J Clin Pharmacol, 42:11S-19S (2002).
Morelli et al., "The effects of cannabidiol and its synergism with bortezomib in multiple myeloma cell lines. A role for transient receptor potential Vanilloid type-2," Blood, 110(9):3281-3290 (2014).
Nabissi et al., "Cannabinoids synergize with carfilzomib, reducing multiple myeloma cells viability and migration," Oncotarget, 7:77553 (2016), 15 pages.
Nakagawa et al., "The combined effects of multiple chemotherapeutic agents for malignant glioma cells," J Neurooncol., 84:31-37 (2007).
Nurmikko et al., "Sativex successfully treats neuropathic pain characterised by allodynia: a randomised, double-blind, placebo-controlled clinical trial," Pain, 133(1-3):210-220 (2007). Epub Nov. 7, 2007.
Podell et al., "2015 ACVIM Small Animal Consensus Statement on Seizure Management in Dogs," J Vet Intern Med, 30:477-490 (2016).
Portella et al., "Inhibitory effects of cannabinoid CB1 receptor stimulation on tumor growth and metastatic spreading: actions on signals involved in angiogenesis and metastasis," The FASEB Journal: Official Publication of the Federation of American Societies for Experimental Biology, 17(12):1771-1773 (2003).
Programme of the 10th Reunion Annual Sociedad Espanola de investigation sabre Cannabinoids (10th Annual Meeting of the Spanish Society for the Investigation of Cannabinoids), held in Santander, Nov. 26 to 28, 2009, downloaded from http:///www.seic.es/reunion-anual-seic on Oct. 25, 2016, 9 pages.
Raab et al., "Multiple myeloma," Lancet, 374(9686):324-339 (2009).
Rana et al., "Cannabidiol and Sodium Valproate Demonstrate Pharmacodynamic Synergism in an Acute Mouse 3.479 Model of Generalised Seizures," Poster, presented at the American Epilepsy Society Annual Meeting 2023; Dec. 1-5, 2023; Orlando, FL, USA, 1 page.
Robins et al., "Phase 2 trial of radiation plus high-dose tamoxifen for glioblastoma multiforme:RTOG protocol BR-0021," Neuro-Oncology, vol. 8, Issue 1, pp. 47-52 (2006).
Rosenthaler et al., "Differences in receptor binding affinity of several phytocannabinoids do not explain their effects on neural cell cultures," Neurotoxicol Teratol., 54:89-93 (2016).
Russo & Guy, "A tale of two cannabinoids: the therapeutic rationale for combining tetrahydrocannabinol and cannabidiol," Med Hypotheses, 66(2):234-236 (2006). Epub Oct. 4, 2005.
Sarfaraz et al., "Cannabinoid receptor as a novel target for the treatment of prostate cancer," Cancer Res., 65(5):1635-1641 (2005).
Scott et al., "Enhancing the Activity of Cannabidiol and Other Cannabinoids In Vitro Through Modifications to Drug Combinations and Treatment Schedules," Anticancer Research, 33(10):4373-4380 (2013).
Scott et al., "Anticancer effects of phytocannabinoids used with chemotherapy in leukaemia cells can be improved by altering the sequence of their administration," Int J Oncol., 51(1):369-377 (2017); doi: 10.3892/ijo.2017.4022. Epub May 29, 2017.
Singh et al., Cannabis extract treatment for terminal acute lymphoblastic leukemia with a Philadelphia chromosome mutation,' Case Rep Oncol., 6(3):585-592 (2013). Epub Nov. 28, 2013; doi: 10.1159/000356446.
Snead, "The gamma-hydroxybutyrate model of absence seizures: correlation of regional brain levels of gamma-hydroxybutyric acid and gamma-butyrolactone with spike wave discharges," Neuropharmacology, 30(2):161-7 (1991). doi: 10.1016/0028-3908(91)90199-I.
Soroceanu et al., "The role of ID-1 in modulating brain tumor invasion and dispersal," Neuro-Oncology 11:564, Abstract No. 3, submitted as Exhibit C to Declaration of Sean McCallister and Pierre-Yves Desprez dated Nov. 26, 2012, filed in U.S. Appl. No. 12/600,553, 1 page.
Strasser et al., "Comparison of Orally Administered Cannabis Extract and Delta-9-Tetrahydrocannabinol in Treating Patients With Cancer-Related Anorexia-Cachexia Syndrome: A Multicenter, Phase III, Randomized, Double-Blind, Placebo-Controlled Clinical Trial From the Cannabis-in-Cachexia-Study-Group," J Clin Oncol., 24(21):3394-3400 (2006).
[No Author Listed] The United Kingdom Parliament, Select Committee on Science and Technology Ninth Report (1998) at http://www.parliament.the-stationery-office.co.uk/pa/Id199798/Idsctech/151/15101.htm, 43 pages.
[No Author Listed] The United Kingdom Parliament, Select Committee on Science and Technology Second Report (2001) at http://www.publications.parliament.uk/pa/Id200001/Idselect/ldsctech/50/5001.htm, 10 pages.
Thomas et al., "Evidence that the plant cannabinoid Delta9-tetrahydrocannabivarin is a cannabinoid CBI and CB2 receptor antagonist," Br J Pharmacol., 146(7):917-926 (2005).
Torres et al., "A combined preclinical therapy of cannabinoids and temozolomide against glioma," Mol Cancer Ther., 10(1):90-103 (2011).
Tucker & Friedman, "Effects of cannabinoids on L1210 murine leukemia. 1. Inhibition of DNA synthesis," Res Commun Chem Pathol Pharmacol, 17(4):703-714 (1997).
Twelves et al., "A two-part safety and exploratory efficacy randomized double-blind, placebo-controlled study of a 1:1 ratio of the cannabinoids cannabidiol and delta-9-tetrahydrocannabinol (CBD:THC) plus dose-intense temozolomide in patients with recurrent glioblastoma multiforme (GBM)," Journal of Clinical Oncology, 35(15):2046 (2017). Abstract Only, 3 pages.
Vaccani et al., "Cannabidiol inhibits human glioma cell migration through a cannabinoid receptor-independent mechanism," Br J Pharmacol., 144(8):1032-1036 (2007).
Velasco et al., "Hypothesis: cannabinoid therapy for the treatment of gliomas?" Neuropharmacology, 47:315-323 (2004).

(56) References Cited

OTHER PUBLICATIONS

Velasco et al., "Anticancer mechanisms of cannabinoids," Curr Oncol., 23(S1):S23-S32 (2016).
Verbraecken et al., "Body surface area in normal-weight, overweight, and obese adults. A comparison study," Metabolism, 55(4):515-524 (2006).
Volk et al., "The efficacy and tolerability of levetiracetam in pharmacoresistant epileptic dogs," Vet J, 176:310-319 (2008).
Volk et al., "International Veterinary Epilepsy Task Force consensus reports on epilepsy definition, classification and terminology," BMC Vet Res, 11:182 (2015), 2 pages.
Wahle et al., "Development of tolerance to the anticonvulsant effect of valproate but not to ethosuximide in a rat model of absence epilepsy," Eur J Pharma. May 1990; 181(1-2):1-8.
Whalley, "Cannabis and epilepsy from recreational use to therapeutic use," University of Reading, 2007, 18 pages.
Wiley et al., "Cytosine arabinoside transport and metabolism in acute leukemias and T cell lymphoblastic lymphoma," Journal of Clinical Investigation, 75(2):632-642 (1985).
Wilson et al., "Can pharmaco-electroencephalography help improve survival of central nervous system drugs in early clinical development?" Drug Discov Today, 19(3):282-8 (2014). doi: 10.1016/j.drudis.2013.08.001.
Zhongshi et al., "The New Development of Anti-tumor Drug. Evaluation and Analysis of Drug-Use in Hospitals of China," 4(1), 2004, 8 pages.
U.S. Appl. No. 15/640,033, filed Jun. 30, 2017.
U.S. Appl. No. 16/768,241, filed May 29, 2020.
U.S. Appl. No. 16/959,354, filed Jun. 30, 2020.
U.S. Appl. No. 16/935,005, filed Jul. 21, 2020.
U.S. Appl. No. 17/012,448, filed Sep. 4, 2020.
U.S. Appl. No. 17/050,956, filed Oct. 27, 2020.
U.S. Appl. No. 17/102,109, filed Nov. 23, 2020.
U.S. Appl. No. 17/231,625, filed Apr. 15, 2021.
U.S. Appl. No. 17/296,066, filed May 21, 2021.
U.S. Appl. No. 17/296,076, filed May 21, 2021.
U.S. Appl. No. 17/424,682, filed Jul. 21, 2021.
U.S. Appl. No. 17/426,442, filed Jul. 28, 2021.
U.S. Appl. No. 17/406,401, filed Aug. 19, 2021.
U.S. Appl. No. 17/435,892, filed Sep. 2, 2021.
U.S. Appl. No. 17/606,370, filed Oct. 25, 2021.
U.S. Appl. No. 17/611,824, filed Nov. 16, 2021.
U.S. Appl. No. 17/548,232, filed Dec. 10, 2021.
U.S. Appl. No. 17/585,415, filed Jan. 26, 2022.
U.S. Appl. No. 17/627,946, filed Jan. 18, 2022.
U.S. Appl. No. 17/631,069, filed Jan. 28, 2022.
U.S. Appl. No. 17/638,629, filed Feb. 25, 2022.
U.S. Appl. No. 17/689,607, filed Mar. 8, 2022.
U.S. Appl. No. 17/689,245, filed Mar. 8, 2022.
U.S. Appl. No. 17/768,048, filed Apr. 11, 2022.
U.S. Appl. No. 17/770,435, filed Apr. 20, 2022.
U.S. Appl. No. 17/770,436, filed Apr. 20, 2022.
U.S. Appl. No. 17/771,184, filed Apr. 22, 2022.
U.S. Appl. No. 17/771,190, filed Apr. 22, 2022.
U.S. Appl. No. 17/771,195, filed Apr. 22, 2022.
U.S. Appl. No. 17/771,183, filed Apr. 22, 2022.
U.S. Appl. No. 17/744,224, filed May 13, 2022.
U.S. Appl. No. 17/777,734, filed May 18, 2022.
U.S. Appl. No. 17/777,677, filed May 18, 2022.
U.S. Appl. No. 17/777,681, filed May 18, 2022.
U.S. Appl. No. 17/841,167, filed Jun. 15, 2022.
U.S. Appl. No. 17/786,949, filed Jun. 17, 2022.
U.S. Appl. No. 17/853,367, filed Jun. 29, 2022.
U.S. Appl. No. 17/817,753, filed Aug. 5, 2022.
U.S. Appl. No. 18/002,437, filed Dec. 19, 2022.
U.S. Appl. No. 18/005,838, filed Jan. 17, 2023.
U.S. Appl. No. 18/005,841, filed Jan. 17, 2023.
U.S. Appl. No. 18/005,843, filed Jan. 17, 2023.
U.S. Appl. No. 18/005,845, filed Jan. 17, 2023.
U.S. Appl. No. 18/005,847, filed Jan. 17, 2023.
U.S. Appl. No. 18/005,848, filed Jan. 17, 2023.
U.S. Appl. No. 18/005,851, filed Jan. 18, 2023.
U.S. Appl. No. 18/005,852, filed Jan. 18, 2023.
U.S. Appl. No. 18/005,853, filed Jan. 18, 2023.
U.S. Appl. No. 18/005,868, filed Jan. 18, 2023.
U.S. Appl. No. 18/005,959, filed Jan. 18, 2023.
U.S. Appl. No. 18/005,960, filed Jan. 18, 2023.
U.S. Appl. No. 18/005,961, filed Jan. 18, 2023.
U.S. Appl. No. 18/006,121, filed Jan. 19, 2023.
U.S. Appl. No. 18/006,125, filed Jan. 19, 2023.
U.S. Appl. No. 18/006,127, filed Jan. 19, 2023.
U.S. Appl. No. 18/006,129, filed Jan. 19, 2023.
U.S. Appl. No. 18,006,131, filed Jan. 19, 2023.
U.S. Appl. No. 18/006,133, filed Jan. 19, 2023.
U.S. Appl. No. 18/161,603, filed Jan. 30, 2023.
U.S. Appl. No. 18/170,235, filed Feb. 16, 2023.
U.S. Appl. No. 18/043,810, filed Mar. 2, 2023.
U.S. Appl. No. 18/044,941, filed Mar. 10, 2023.
U.S. Appl. No. 18/245,856, filed Mar. 17, 2023.
U.S. Appl. No. 18/186,792, filed Mar. 20, 2023.
U.S. Appl. No. 18/311,221, filed May 2, 2023.
U.S. Appl. No. 18/256,307, filed Jun. 7, 2023.
U.S. Appl. No. 18/257,373, filed Jun. 14, 2023.
U.S. Appl. No. 18/257,537, filed Jun. 14, 2023.
U.S. Appl. No. 18/257,479, filed Jun. 14, 2023.
U.S. Appl. No. 18/258,485, filed Jun. 20, 2023.
U.S. Appl. No. 18/446,405, filed Aug. 8, 2023.
U.S. Appl. No. 18/546,254, filed Aug. 11, 2023.
U.S. Appl. No. 18/548,003, filed Aug. 25, 2023.
U.S. Appl. No. 18/477,467, filed Sep. 28, 2023.
U.S. Appl. No. 18/479,671, filed Oct. 2, 2023.
U.S. Appl. No. 18/560,316, filed Nov. 10, 2023.
U.S. Appl. No. 18/560,337, filed Nov. 10, 2023.
U.S. Appl. No. 18/560,341, filed Nov. 10, 2023.
U.S. Appl. No. 18/560,346, filed Nov. 10, 2023.
U.S. Appl. No. 18/526,795, filed Dec. 1, 2023.
U.S. Appl. No. 18/545,754, filed Dec. 19, 2023.
U.S. Appl. No. 18/292,844, filed Jan. 26, 2024.
U.S. Appl. No. 18/597,717, filed Mar. 6, 2024.

\* cited by examiner

Maximum seizure severity of the CBDV (-/-) BDS in the PTZ model of epilepsy

Percentage mortality of the CBDV (-/-) BDS in the PTZ model of epilepsy

Percentage of animals that were seizure free in the CBDV (-/-) BDS in the PTZ model of epilepsy Latency to seizure onset in the CBDV (-/-) BDS in the PTZ model of epilepsy Percentage of animals that experienced tonic-clonic seizures in the CBDV (-/-) BDS in the PTZ model of epilepsy

PHARMACEUTICAL COMPOSITION COMPRISING THE PHYTOCANNABINOIDS CANNABIDIVARIN (CBDV) AND CANNABIDIOL (CBD)

CROSS-REFERENCE TO RELATED APPLICATIONS

This application is a continuation of U.S. patent application Ser. No. 16/709,401, filed on Dec. 10, 2019, which is a continuation of U.S. patent application Ser. No. 14/345,968, filed on Sep. 14, 2012, now U.S. Pat. No. 10,729,665, which is a national stage application under 35 U.S.C. § 371 of International Application No. PCT/GB2012/052284, filed internationally on Sep. 14, 2012, which claims priority to United Kingdom Application No. 1116789.7, filed Sep. 29, 2011, which are incorporated herein by reference in their entirety.

This invention relates to a pharmaceutical composition comprising or consisting essentially of the phytocannabinoids cannabidivarin (CBDV) and cannabidiol (CBD).

The composition is particularly safe and efficacious for use in the treatment of neurological conditions, characterized by hyper-excitability of the central nervous system, convulsions or seizures such as occur in epilepsy.

Preferably the CBDV and the CBD are present with at least one non-cannabinoid component of cannabis such as one or more terpenes or a terpene fraction.

More particularly the composition further comprises one or more cannabichromene type compounds. Particularly cannabichromene propyl variant (CBCV) and/or cannabichromene (CBC).

More particularly still the composition is absent or substantially absent of other cannabinoids, including in particular tetrahydrocannabinol (THC) and tetrahydrocannabivarin (THCV), which would normally be present in significant amounts in cannabis chemotypes bred to contain a significant amount of CBDV and/or CBD.

BACKGROUND

Epilepsy is a chronic neurological disorder presenting a wide spectrum of diseases that affects approximately 50 million people worldwide (Sander, 2003). Advances in the understanding of the body's internal 'endocannabinoid' system has lead to the suggestion that cannabis-based medicines may have the potential to treat this disorder of hyper-excitability in the central nervous system (Mackie, 2006, Wingerchuk, 2004, Alger, 2006).

Cannabis has been ascribed both pro-convulsant (Brust et al., 1992) and anti-convulsant effects. Therefore, it remains to determine whether cannabinoids represent a yet to be unmasked therapeutic anticonvulsant or, conversely, a potential risk factor to recreational and medicinal users of cannabis (Ferdinand et al., 2005).

In 1975 Consroe et al. described the case of young man whose standard treatment (phenobarbital and phenytoin), didn't control his seizures. When he began to smoke cannabis socially he had no seizures. However when he took only cannabis the seizures returned. They concluded that 'marihuana may possess an anti-convulsant effect in human epilepsy'.

A study by Ng (1990) involved a larger population of 308 epileptic patients who had been admitted to hospital after their first seizure. They were compared to a control population of 294 patients who had not had seizures, and it was found that using cannabis seemed to reduce the likelihood of having a seizure. However this study was criticized in an Institute of Medicine report (1999) which claimed it was 'weak', as 'the study did not include measures of health status prior to hospital admissions and differences in their health status might have influenced their drug use' rather than the other way round.

Three controlled trials have investigated the anti-epilepsy potential of cannabidiol. In each, cannabidiol was given in oral form to sufferers of generalised grand mal or focal seizures.

Cunha et al (1980) reported a study on 16 grand mal patients who were not doing well on conventional medication. They received their regular medication and either 200-300 mg of cannabidiol or a placebo. Of the patients who received CBD, 3 showed complete improvement, 2 partial, 2 minor, while 1 remained unchanged. The only unwanted effect was mild sedation. Of the patients who received the placebo, 1 improved and 7 remained unchanged.

Ames (1986) reported a less successful study in which 12 epileptic patients were given 200-300 mg of cannabidiol per day, in addition to standard antiepileptic drugs. There seemed to be no significant improvement in seizure frequency.

Trembly et al (1990) performed an open trial with a single patient who was given 900-1200 mg of cannabidiol a day for 10 months. Seizure frequency was markedly reduced in this single patient.

In addition to the disclosures suggesting CBD may be beneficial there is a report (Davis & Romsey) of tetrahydrocannabinol (THC) being administered to 5 institutionalized children who were not responding to their standard treatment (phenobarbital and phenoytin). One became entirely free of seizures, one became almost completely free of seizures, and the other three did no worse than before.

In WO 2006/054057 it is suggested that the cannabinoid tetrahydrocannabivarin (THCV) may behave as anti-epileptic. However the main teaching in this document is the determination that THCV acts as a CB1 antagonist.

The application WO 2007/138322 shows CBD to be an inverse agonist at the CB1 and CB2 receptors and suggests this compound and structurally related compounds including CBDV, may have a therapeutic benefit in a wide range of conditions which involve these receptors. More specifically the data demonstrates that the cannabinoid CBD reduced bodyweight in rats.

However other work on cannabinoids has shown that despite THCV's structural similarity to THC the two compounds behave quite differently at the CB1 receptor and consequently it does not follow that the propyl cannabinoid analogs will behave as their pentyl equivalents.

In addition a study in 2007 by Deshpande et al. established that the CB1 antagonist rimonabant was a pro-convulsant; this study demonstrated that antagonism of the CB1 receptor caused epileptic activity. The inference from this study is that cannabinoids which act as antagonists of the CB1 receptor may not be useful as anti-convulsants; indeed they may exacerbate such a condition.

The application WO 2007/083098 describes the use of cannabis plant extracts with neuroprotective properties. Cannabinoid extracts containing THC and CBD were shown to be more effective than their pure counterparts in this area of medicine.

The application WO 02/064109 describes a pharmaceutical formulation where the cannabinoids THC and CBD are used. The application goes on to state that the propyl analogs of these cannabinoids may also be used in the formulation. Since this application was written it has been shown that THCV behaves in a very different manner to THC and therefore the assumption that the propyl analogs of cannabinoids may behave in a similar manner to their pentyl counterparts is now not valid.

The application GB2471565 describes the use of THCV for the treatment of generalised seizures; it also describes the use of CBD in combination with THCV.

The application GB1005364.3 (unpublished) describes the use of CBDV for use in the treatment of epilepsy.

The condition of epilepsy is a very difficult to treat disease, there are more than forty recognisable types of epileptic syndrome partly due to seizure susceptibility varying from patient to patient (McCormick and Contreras, 2001, Lutz, 2004) and a challenge is finding drugs which are effective against these differing types.

Neuronal activity is a prerequisite for proper brain function. However, disturbing the excitatory—inhibitory equilibrium of neuronal activity may induce epileptic seizures. These epileptic seizures can be grouped into two basic categories:
  a) partial, and
  b) generalised seizures.

Partial seizures originate in specific brain regions and remain localised—most commonly the temporal lobes (containing the hippocampus), whereas generalised seizures appear in the entire forebrain as a secondary generalisation of a partial seizure (McCormick and Contreras, 2001, Lutz, 2004). This concept of partial and generalised seizure classification did not become common practice until the International League Against Epilepsy published a classification scheme of epileptic seizures in 1969 (Merlis, 1970, Gastaut, 1970, Dreifuss et al., 1981).

The International League Against Epilepsy further classified partial seizures, separating them into simple and complex, depending on the presence or the impairment of a consciousness state (Dreifuss et al., 1981).

The League also categorized generalised seizures into numerous clinical seizure types, some examples of which are outlined below:

Absence seizures occur frequently, having a sudden onset and interruption of ongoing activities. Additionally, speech is slowed or impeded with seizures lasting only a few seconds (Dreifuss et al., 1981).

Tonic-clonic seizures, often known as "grand mal", are the most frequently encountered of the generalised seizures (Dreifuss et al., 1981). This generalised seizure type has two stages: tonic muscle contractions which then give way to a clonic stage of convulsive movements. The patient remains unconscious throughout the seizure and for a variable period of time afterwards.

Atonic seizures, known as "drop attacks", are the result of sudden loss of muscle tone to either a specific muscle, muscle group or all muscles in the body (Dreifuss et al., 1981).

The onset of epileptic seizures can be life threatening with sufferers also experiencing long-term health implications (Lutz, 2004). These implications may take many forms:
  mental health problems (e.g. prevention of normal glutamatergic synapse development in childhood);
  cognitive deficits (e.g. diminishing ability of neuronal circuits in the hippocampus to learn and store memories); and
  morphological changes (e.g. selective loss of neurons in the CA1 and CA3 regions of the hippocampus in patients presenting mesial temporal lobe epilepsy as a result of excitotoxicity) (Swann, 2004, Avoli et al., 2005)

It is noteworthy that epilepsy also greatly affects the lifestyle of the sufferer—potentially living in fear of consequential injury (e.g. head injury) resulting from a grand mal seizure or the inability to perform daily tasks or the inability to drive a car unless having had a lengthy seizure-free period (Fisher et al., 2000).

Despite the historic work on CBD in epilepsy in the 1980's/1990's, research in the field of anti-convulsants has focused on many other candidates many of which are now approved for use in the treatment of epilepsy. Such drugs include: acetozolamide, carbamazepine, clobazam, clonazepam, ethosuximide, eslicarbazepine acetate, gabapentin, lacosamide, lamotriquine, levetiracetam, oxcarbazepine, phenobarbital, phenytoin, pregabalin, primidone, rufinamide, sodium valproate, tiagabine, topiramate, valproate, vigabatrin, and zonisamide.

The mode of action of some of these is understood and for others is unknown. Some modes of action are set out in Table 1 below: (Adapted from: Schachter S C. Treatment of seizures. In: Schachter S C, Schomer D L, eds. The comprehensive evaluation and treatment of epilepsy. San Diego, CA: Academic Press; 1997. p. 61-74)

TABLE 1

| Antiepileptic drug | Mechanism of action | Sodium or calcium or GABA channel involvement |
| --- | --- | --- |
| Barbiturates: primidone (Mysoline), phenobarbital | Enhances GABAergic inhibition | GABA |
| Carbamazepine (Tegretol, Tegretol-XR, Carbatrol) | Inhibits voltage-dependent sodium channels | Sodium |
| Ethosuximide (Zarontin) | Modifies low-threshold or transient neuronal calcium currents | Calcium |
| Felbamate (Felbatol) | Unknown | |
| Gabapentin (Neurontin) | Unknown | |
| Lamotrigine (Lamictal) | Inhibits voltage-dependent sodium channels, resulting in decreased release of the excitatory neurotransmitters glutamate and aspartate | Sodium |
| Phenytoin (Dilantin, Phenytek) | Blocks sodium-dependent action potentials; reduces neuronal calcium uptake | Sodium/Calcium |

TABLE 1-continued

| Antiepileptic drug | Mechanism of action | Sodium or calcium or GABA channel involvement |
|---|---|---|
| Valproate (Depakote, Depakote ER, Depakene, valproic acid) | Reduces high-frequency neuronal firing and sodium-dependent action potentials; enhances GABA effects | Sodium/GABA |

However despite the introduction of some twenty different compounds for treatment of epilepsy over the last twenty years there remains a need for alternate drugs for several reasons:

i) 1-2% of the world's population suffer from epilepsy (http.//www.ncbi.nlm.nih.gov/sites/ppmc/articles/PMC1808496/);
ii) Of these 30% are refractory to existing treatments; and
iii) There are also notable motor side effects in the existing therapies (http://en.wikipedia.org/wiki/Epilepsy).

For example valproate and ethosuximide both exhibit notable motor and other side effects (including sedation) when given to rats at doses greater than 200 mg/kg, as does phenobarbital at doses greater than 250 mg/kg in rat models of epilepsy.

Three well-established and extensively used in vivo models of epilepsy are:

pentylenetetrazole-induced (PTZ) model of generalised seizures (Obay et al., 2007, Rauca et al., 2004);
pilocarpine-induced model of temporal lobe (i.e. hippocampus) seizures (Pereira et al., 2007); and
penicillin-induced model of partial seizures (Bostanci and Bagirici, 2006).

These provide a range of seizure and epilepsy models, essential for therapeutic research in humans.

In the foregoing specification the following terms are used and are intended to have the following meanings/definitions:

"Cannabinoids" are a group of compounds including the endocannabinoids, the phytocannabinoids and those which are neither endocannabinoids or phytocannabinoids, hereafter "syntho-cannabinoids".

"Endocannabinoids" are endogenous cannabinoids, which are high affinity ligands of CB1 and CB2 receptors.

"Phytocannabinoids" are cannabinoids that originate in nature and can be found in the cannabis plant. The phytocannabinoids can be present in an extract including a botanical drug substance, isolated, or reproduced synthetically.

"Syntho-cannabinoids" are those compounds capable of interacting with the cannabinoid receptors (CB1 and/or CB2) but are not found endogenously or in the cannabis plant. Examples include WIN 55212 and rimonabant.

An "isolated phytocannabinoid" is one which has been extracted from the cannabis plant and purified to such an extent that all the additional components such as secondary and minor cannabinoids and the non-cannabinoid fraction have been removed.

A "synthetic cannabinoid" is one which has been produced by chemical synthesis this term includes modifying an isolated phytocannabinoid, by for example forming a pharmaceutically acceptable salt thereof.

A "botanical drug substance" or "BDS" is defined in the Guidance for Industry Botanical Drug Products Draft Guidance, August 2000, US Department of Health and Human Services, Food and Drug Administration Centre for Drug Evaluation and Research as: "A drug derived from one or more plants, algae, or microscopic fungi. It is prepared from botanical raw materials by one or more of the following processes: pulverisation, decoction, expression, aqueous extraction, ethanolic extraction or other similar processes." A botanical drug substance does not include a highly purified or chemically modified substance derived from natural sources. Thus, in the case of cannabis, BDS derived from cannabis plants do not include highly purified Pharmacopoeial grade cannabinoids.

In the present invention a BDS is considered to have two components: the phytocannabinoid-containing component and the non-phytocannabinoid containing component.

Preferably the phytocannabinoid-containing component is the larger component comprising greater than 50% (w/w) of the total BDS and the non-phytocannabinoid containing component is the smaller component comprising less than 50% (w/w) of the total BDS.

The amount of phytocannabinoid-containing component in the BDS may be greater than 55%, through 60%, 65%, 70%, 75%, 80% to 85% or more of the total extract. The actual amount is likely to depend on the starting material used and the method of extraction used.

The "principle phytocannabinoid" in a BDS is the phytocannabinoid that is present in an amount that is higher than that of the other phytocannabinoids. Preferably the principle phytocannabinoid is present in an amount greater than 40% (w/w) of the total extract. More preferably the principle phytocannabinoid is present in an amount greater than 50% (w/w) of the total extract. More preferably still the principle phytocannabinoid is present in an amount greater than 60% (w/w) of the total extract.

The amount of the principle phytocannabinoid in the BDS is preferably greater than 50% of the phytocannabinoid-containing fraction, more preferably still greater than 55% of the phytocannabinoid-containing fraction, and more preferably still greater than 60% through 65%, 70%, 75%, 80%, 85%, 90% and 95% of the phytocannabinoid-containing fraction.

The "secondary phytocannabinoid/s" in a BDS is the phytocannabinoid/s that is/are present in significant proportions. Preferably the secondary phytocannabinoid is present in an amount greater than 5% (w/w) of the total extract, more preferably greater than 10% (w/w) of the total extract, more preferably still greater than 15% (w/w) of the total extract. Some BDS's will have two or more secondary phytocannabinoids that are present in significant amounts. However not all BDS's will have a secondary phytocannabinoid.

The "minor phytocannabinoid/s" in a BDS can be described as the remainder of all the phytocannabinoid components once the principle and secondary phytocannabinoids are accounted for. Preferably the minor phytocannabinoids are present in total in an amount of less than 5% (w/w) of the total extract, and most preferably the minor phytocannabinoid is present in an amount less than 2% (w/w) of the total extract.

The term "absent" or "substantially absent" refers to less than 1%, preferably less than 0.5%, more preferably still less than 0.3%, most preferably less than 0.1% (w/w) of total extract.

The term "consisting essentially of" is limited to the phytocannabinoids which are specified, it does not exclude non-cannabinoid components that may also be present.

Typically the non-phytocannabinoid containing component of the BDS comprises terpenes, sterols, triglycerides, alkanes, squalenes, tocopherols and carotenoids.

These compounds may play an important role in the pharmacology of the BDS either alone or in combination with the phytocannabinoid.

The "terpene fraction" may be of significance and can be broken down by the type of terpene: monoterpene or sesquiterpene. These terpene components can be further defined in a similar manner to the cannabinoids.

The amount of non-phytocannabinoid containing component in the BDS may be less than 45%, through 40%, 35%, 30%, 25%, 20% to 15% or less of the total extract. The actual amount is likely to depend on the starting material used and the method of extraction used.

The "principle monoterpene/s" in a BDS is the monoterpene that is present in an amount that is higher than that of the other monoterpenes. Preferably the principle monoterpene/s is present in an amount greater than 20% (w/w) of the total terpene content. More preferably the principle monoterpene is present in an amount greater than 30% (w/w) of the total terpene content, more preferably still greater than 40% (w/w) of the total terpene content, and more preferably still greater than 50% (w/w) of the total terpene content. The principle monoterpene is preferably a myrcene or pinene. In some cases there may be two principle monoterpenes. Where this is the case the principle monoterpenes are preferably a pinene and/or a myrcene.

The "principle sesquiterpene" in a BDS is the sesquiterpene that is present in an amount that is higher than all the other sesquiterpenes. Preferably the principle sesquiterpene is present in an amount greater than 20% (w/w) of the total terpene content, more preferably still greater than 30% (w/w) of the total terpene content. The principle sesquiterpene is preferably a caryophyllene and/or a humulene.

The sesquiterpene components may have a "secondary sesquiterpene". The secondary sesquiterpene is preferably a pinene, which is preferably present at an amount greater than 5% (w/w) of the total terpene content, more preferably the secondary sesquiterpene is present at an amount greater than 10% (w/w) of the total terpene content.

The secondary sesquiterpene is preferably a humulene which is preferably present at an amount greater than 5% (w/w) of the total terpene content, more preferably the secondary sesquiterpene is present at an amount greater than 10% (w/w) of the total terpene content.

Alternatively botanical extracts may be prepared by introducing isolated phytocannabinoids or their synthetic equivalent into a non-cannabinoid plant fraction as can be obtained from a zero cannabinoid plant or one or more non-cannabinoid components found in the cannabis plant such as terpenes.

The structures of the phytocannabinoids CBDV, CBD, CBCV, CBC, THCV and THC are as shown below:

CBDV     Cannabidivarin

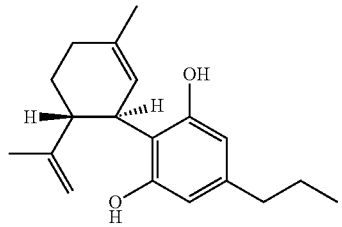 [SMILES: C=C(C)[C@@H]1CCC(C)=C[C@H]1c1c(O)cc(CCC)cc1O]

CBD     Cannabidiol

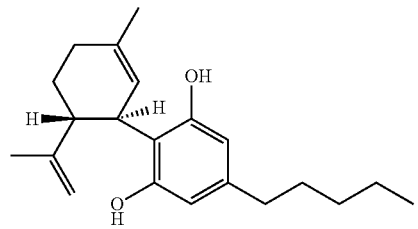 [SMILES: C=C(C)[C@@H]1CCC(C)=C[C@H]1c1c(O)cc(CCCCC)cc1O]

CBCV     Cannabichromene propyl variant

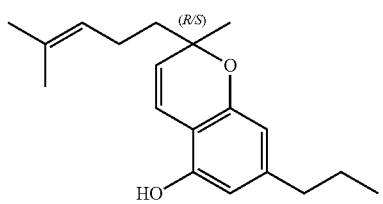 [SMILES: CCCc1cc(O)c2c(c1)OC(C)(CCC=C(C)C)C=C2]

| | | |
|---|---|---|
| CBC | Cannabichromene | 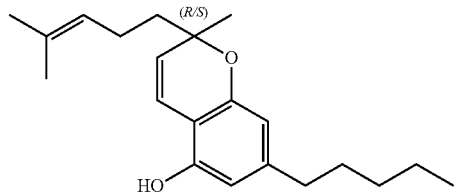 [SMILES: CCCCCc1cc(O)c2c(c1)OC(C)(CCC=C(C)C)C=C2] |
| THCV | Tetrahydrocannabivarin | 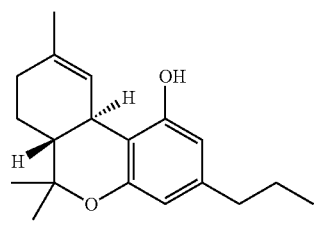 [SMILES: CCCc1cc(O)c2c(c1)OC(C)(C)[C@@H]1CCC(C)=C[C@@H]21] |
| THC | Tetrahydrocannabinol | 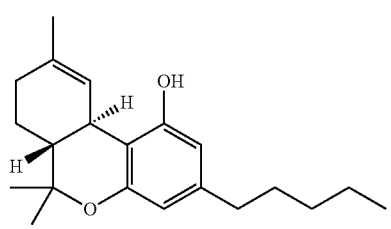 [SMILES: CCCCCc1cc(O)c2c(c1)OC(C)(C)[C@@H]1CCC(C)=C[C@@H]21] |

Phytocannabinoids can be found as either the neutral (decarboxylated form) or the carboxylic acid form depending on the method used to extract the cannabinoids. For example it is known that heating the carboxylic acid form will cause most of the carboxylic acid form to decarboxylate into the neutral form.

Where a synthetic phytocannabinoid is used the term is intended to include compounds, metabolites or derivatives thereof, and pharmaceutically acceptable salts of such compounds.

The term "pharmaceutically acceptable salts" refers to salts or esters prepared from pharmaceutically acceptable non-toxic bases or acids, including inorganic bases or acids and organic bases or acids, as would be well known to persons skilled in the art. Many suitable inorganic and organic bases are known in the art.

Phytocannabinoids can occur as either the pentyl (5 carbon atoms) or propyl (3 carbon atoms) variant. Initially it was thought that the propyl and pentyl variants would have similar properties, however recent research suggests this is not true. For example the phytocannabinoid THC is known to be a CB1 receptor agonist whereas the propyl variant THCV has been discovered to be a CB1 receptor antagonist meaning that it has almost opposite effects. This is confirmed by Pertwee (2000) in Cannabinoid receptor ligands: clinical and neuropharmacological considerations relevant to future drug discovery and development.

It is an object of the present invention to identify compositions which are safe and efficacious for use in the treatment of neurological conditions, characterized by hyper-excitability of the central nervous system, convulsions or seizures such as occur in epilepsy.

Indeed, a major drawback with existing standard anti-epileptic drugs (SAEDs) is that 30% are refractory to existing treatments and there are also notable motor side effects in the existing therapies. Thus it is desirable to use compounds or combinations which reduce or are absent of such side effects.

BRIEF SUMMARY OF THE DISCLOSURE

In accordance with a first aspect of the present invention there is provided a composition comprising or consisting essentially of the phytocannabinoids cannabidivarin (CBDV) and cannabidiol (CBD).

Preferably the composition further comprising one or more excipients.

Preferably the composition further comprises at least one non-cannabinoid component of cannabis. More preferably the at least one non-cannabinoid component of cannabis is or comprises a terpene.

With reference to terpenes it should be noted that terpenes can be classified further into monoterpenes or sesquiterpenes. Common monoterpenes found in cannabis include myrcene and pinene and common sesquiterpenes found in cannabis include caryophyllenes and humulene.

Preferably the composition comprises or consists essentially of CBDV, CBD and one or more cannabichromene type compounds. More preferably the one or more cannabichromene type compounds is cannabichromene propyl variant (CBCV) and/or cannabichromene (CBC).

Preferably the composition is absent or substantially absent of any other cannabinoids. More preferably the composition is absent or substantially absent of the cannabinoids tetrahydrocannabivarin (THCV) and/or tetrahydrocannabinol (THC).

In particular the composition should comprise less than 0.3% (w/w) THC.

Preferably the composition comprises or consists essentially of the cannabinoids CBDV and CBD in a ratio of from 7:1 to 1:2 (CBDV:CBD). More preferably the CBDV and CBD are present in a ratio of from 5:1 to 1:1 (CBDV:CBD).

More preferably still the CBDV and CBD are present in a ratio of 4.5:1 to 2:1 (CBDV:CBD).

Preferably the composition is packaged for delivery in a unit dosage form. More preferably the unit dosage form comprises from 500 to 2000 mg CBDV and from 100 to 600 mg CBD.

A "unit dose" is herein defined as a maximum dose of medication that can be taken at any one time or within a specified dosage period such as for example, 4 hours.

In a further embodiment of the present invention the composition further comprises a standard anti-epileptic drug (SAED).

A standard anti-epileptic drug is a medicament with anti-convulsant activity that is or has been used in the treatment of epilepsy.

In accordance with a second aspect of the present invention there is provided an extract or BDS comprising the phytocannabinoids CBDV and CBD but substantially absent of the cannabinoids THCV and THC.

The cannabinoids THCV and THC may not desirable components of a composition for use in the treatment of epilepsy for several reasons. In the case of THCV the fact that this phytocannabinoid is a known CB1 receptor antagonist gives rise to questions over the appropriateness of THCV for use in the treatment of epilepsy, particularly when one considers the evidence provided by Deshpande et al. that CB1 antagonists may be pro-convulsant and may give rise to suicidal tendencies. In the case of THC it is not clearly known whether THC is a pro- or anti-convulsant, however it is widely acknowledged that some of the side effects caused by THC, such as psychosis and anxiety, are particularly undesirable.

Preferably the extract or BDS further comprises one or more non-cannabinoid component(s).

In accordance with a third aspect of the present invention there is provided a combination of the phytocannabinoids cannabidivarin (CBDV) and cannabidiol (CBD) for use in the treatment of neurological conditions, characterised by hyper-excitability of the central nervous system, convulsions or seizures.

Preferably the combination of the the neurological condition is epilepsy. More preferably the type of epilepsy to be treated is generalised seizure.

Preferably the combination of the phytocannabinoids cannabidivarin (CBDV) and cannabidiol (CBD) further comprises a standard anti-epileptic drug (SAED).

Preferably the combination of the phytocannabinoids CBDV and CBD are absent or substantially absent of any other cannabinoids. More preferably the composition is absent or substantially absent of the cannabinoids tetrahydrocannabivarin (THCV) and/or tetrahydrocannabinol (THC).

In accordance with a fourth aspect of the present invention there is provided the use of a combination of the phytocannabinoids cannabidivarin (CBDV) and cannabidiol (CBD) in the manufacture of a medicament for use in the treatment of neurological conditions, characterised by hyper-excitability of the central nervous system, convulsions or seizures.

Preferably the medicament is absent or substantially absent of any other cannabinoids. More preferably the composition is absent or substantially absent of the cannabinoids tetrahydrocannabivarin (THCV) and/or tetrahydrocannabinol (THC).

In accordance with a fifth aspect of the present invention there is provided a method for the treatment of neurological conditions, characterised by hyper-excitability of the central nervous system, convulsions or seizures, which comprises administering to a subject in need thereof a therapeutically effective amount of a combination of the phytocannabinoids cannabidivarin (CBDV) and cannabidiol (CBD).

Preferably the therapeutically effective amount of a combination of the phytocannabinoids cannabidivarin (CBDV) and cannabidiol (CBD) is absent or substantially absent of any other cannabinoids. More preferably the composition is absent or substantially absent of the cannabinoids tetrahydrocannabivarin (THCV) and/or tetrahydrocannabinol (THC).

BRIEF DESCRIPTION OF THE DRAWINGS

Embodiments of the invention are further described hereinafter with reference to the accompanying drawings, in which.

Figure 1:
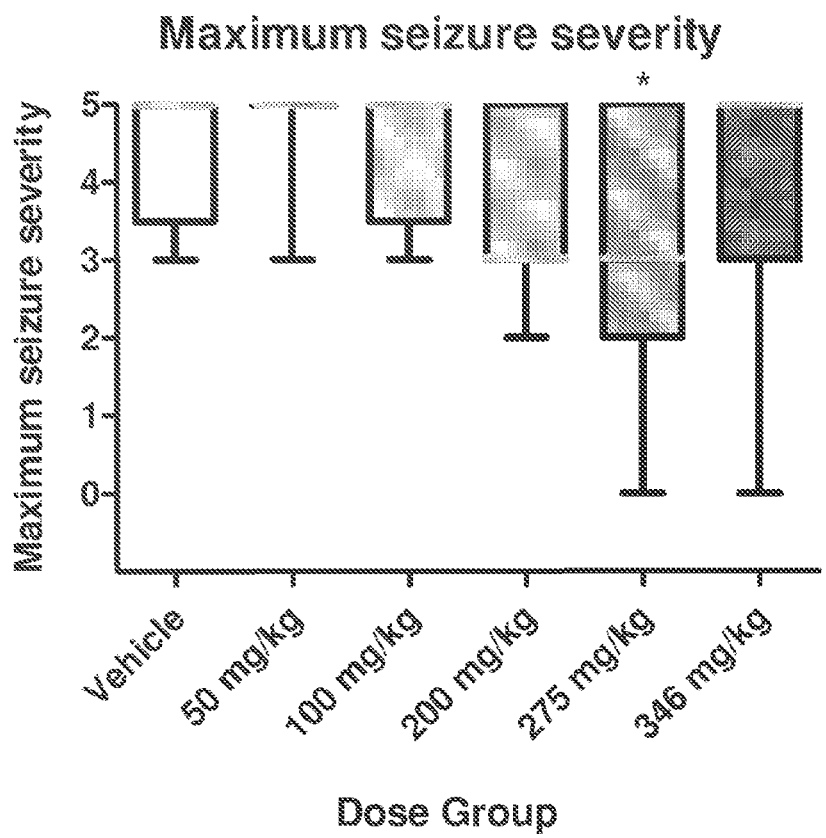
FIG. 1 shows the maximum seizure severity of the CBDV (–/–) BDS in the PTZ model of epilepsy.

The CBDV (–/–) BDS is used to designate a CBDV BDS from which THCV and THC have been selectively removed.

DETAILED DESCRIPTION

Example 1 below describes the use of a CBDV botanical drug substance (BDS) from which the cannabinoids THCV and THC have been selectively removed, hereinafter CBDV (–/–) BDS. The PTZ model of generalized seizures in epilepsy was used to determine the anti-convulsant activity of the test article.

Example 1

Use of a Composition Comprising CBDV and CBD in the PTZ Model of Generalised Seizures
Methodology:
Animals:

Male Wistar rats (P24-29; 75-110 g) were used to assess the combined effect of a composition comprising the phytocannabinoids CBDV and CBD in the PTZ model of generalised seizures. Animals were habituated to the test environment, cages, injection protocol and handling prior to experimentation. Animals were housed in a room at 21° C. on a 12 hour light:dark cycle (lights on 0900) in 50% humidity, with free access to food and water.

The human dose equivalent (HED) can be estimated using the following formula:

$$HED = \text{Animal dose}\,(\text{mg/kg}) \text{ multiplied by } \frac{\text{Animal } K_m}{\text{Human } K_m}$$

The $K_m$ for a rat is 6 and the $K_m$ for a human is 37.

Thus, for a human of approx 60 Kg a 200 mg/Kg dose in rat would equate to a human daily dose of about 2000 mg.
Composition A composition was prepared using a CBDV botanical drug substance (BDS) that had been further prepared by centrifugal partition chromatography to remove the cannabinoids THCV and THC, such that the cannabinoids consisted essentially of CBDV and CBD, and lesser amounts of CBCV and CBC. This BDS is termed CBDV (−/−) BDS for the purpose of this application.

Experimental Setup:

Five 6 L Perspex tanks with lids were placed on a single bench with dividers between them. Closed-circuit television (CCTV) cameras were mounted onto the dividers to observe rat behaviour. Sony Topica CCD cameras (Bluecherry, USA) were linked via BNC cables to a low-noise PC via Brooktree digital capture cards (Bluecherry, USA). Zoneminder (http://www.zoneminder.com) software was used to monitor rats, start and end recordings and manage video files. In-house Linux scripts were used to encode video files into a suitable format for further offline analysis using The Observer (Noldus Technologies).

PTZ Model:

A range of doses of PTZ (50-100 mg/kg body weight) were used to determine the best dose for induction of seizures. As a result, a dose of 85 mg/kg injected intraperitoneally (IP; stock solution 50 mg/ml in 0.9% saline) were used to screen the CBDV (−/−) BDS test article.

Experimental Protocols:

On the day of testing, the CBDV (−/−) BDS was administered via intra-peritoneal (i.p.) injection at doses of 50, 100, 200, 275 and 346 mg/kg alongside animals that were injected with a matched volume of the cannabinoid vehicle (2:1:17 ethanol:Cremophor:saline), which served as the negative control group, (giving defined doses of CBDV and CBD as set out in Table 1.1 below). Animals were then observed for 1 hour, after which time they received an IP injection of 85 mg/kg PTZ. Negative vehicle controls were performed in parallel with cannabinoid-dosed subjects. After receiving a dose of PTZ, animals were observed and videoed to determine the severity of seizure and latency to several seizure behaviour types (see in vivo analysis, below). Animals were filmed for half an hour after last sign of seizure, and then returned to their cage.

Dose Groups:

Table 1.1 below demonstrates the respective content of the cannabinoids CBDV and CBD in the different dose groups of the CBDV (−/−) BDS.

TABLE 1.1:

| Dose group (amount of test article) | CBDV content (mg/kg) | CBD content (mg/kg) | Ratio (CBDV:CBD) |
| --- | --- | --- | --- |
| Vehicle | 0 | 0 | — |
| 50 mg/kg | 29 | 7 | 4.14:1 |
| 100 mg/kg | 58 | 14 | 4.14:1 |
| 200 mg/kg | 116 | 27 | 4.29:1 |
| 275 mg/kg | 159 | 38 | 4.18:1 |
| 346 mg/kg | 200 | 47 | 4.25:1 |

In Viva Analysis:

Animals were observed during experimental procedures, but all analysis was performed offline on recorded video files using The Observer behavioural analysis software (Noldus, Netherlands). A seizure severity scoring system was used to determine the levels of seizure experienced by subjects (Pohl & Mares, 1987). All signs of seizure were detailed for all animals.

TABLE 1.2

Seizure severity scoring scale, adapted from Pohl & Mares, 1987.

| Seizure score | Behavioural expression | Righting reflex |
| --- | --- | --- |
| 0 | No changes to behaviour | Preserved |
| 0.5 | Abnormal behaviour (sniffing, excessive washing, orientation) | Preserved |
| 1 | isolated myoclonic jerks | Preserved |
| 2 | Atypical clonic seizure | Preserved |
| 3 | Fully developed bilateral forelimb clonus | Preserved |
| 3.5 | Forelimb clonus with tonic component and body twist | Preserved |
| 4 | Tonic-clonic seizure with suppressed tonic phase | Lost |
| 5 | Fully developed tonic-clonic seizure | Lost |
| 6 | Death | |

Latency from Injection of PTZ to Specific Indicators of Seizure Development:

The latency (in seconds) from injection of PTZ to first myoclonic jerk (FMJ; score of 1), and to the animal attaining "forelimb clonus with tonic component and body twist" (score of 3.5) were recorded. FMJ is an indicator of the onset of seizure activity, whilst >90% of animals developed scores of 3.5, and so is a good marker of the development of more severe seizures. Data are presented as the mean±S.E.M. within an experimental group.

Maximum Seizure Severity:

This is given as the median value for each experimental group based on the scoring scale below.

Percentage Mortality:

The percentage of animals within an experimental group that died as a result of PTZ-induced seizures. Note that the majority of animals that developed tonic-clonic seizures (scores of 4 and 5) died as a result, and that a score of 6 (death) automatically denotes that the animal also experienced tonic-clonic seizures.

Seizure Duration:

The time (in seconds) from the first sign of seizure (typically FMJ) to either the last sign of seizure or, in the case of subjects that died, the time of death—separated into animals that survived and those that did not. This is given as the mean±S.E.M. for each experimental group.

Statistics:

For measures of latency and severity, one way analysis of variance (ANOVA) was performed on all the groups together in order to detect overall effects of the test article ($p \leq 0.05$ considered significant), and is denoted by a '*' in the figures.

Significant ANOVA results were followed by post hoc tests to test differences between vehicle and drug groups (Tukey's test, $p \leq 0.05$ considered significant), and is denoted by a '*' in the figures.

Results:

FIG. 1 illustrates the maximum seizure severity, a significant effect of the CBDV (−/−) BDS on the maximum seizure severity was observed at a dose of 275 mg/kg CBDV (−/−) BDS.

Figure 2:
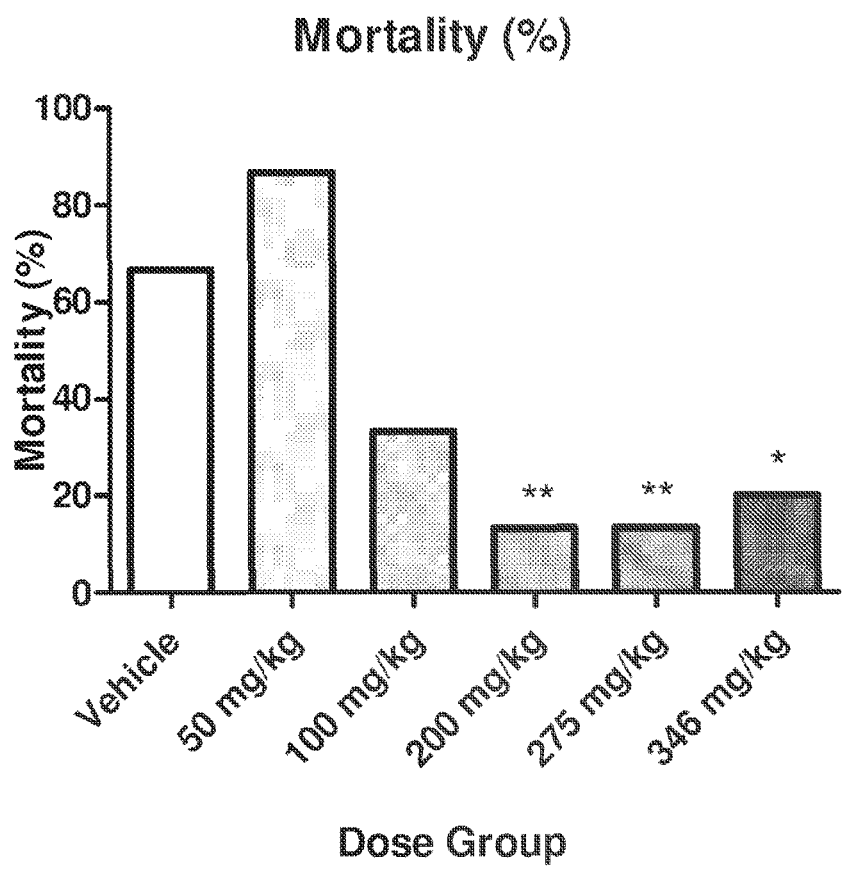
FIG. 2 shows the percentage mortality of the CBDV (–/–) BDS in the PTZ model of epilepsy.

FIG. 2 illustrates the percentage mortality of the animals dosed with the CBDV (−/−) BDS. As can be observed the animals given the, 200 and 275 mg/kg CBDV (−/−) BDS had a strongly statistical significance and the animals given the highest dose (346 mg/kg CBDV (−/−) BDS had a less statistical significance but still resulted in a decrease in the percentage mortality.

Figure 3:
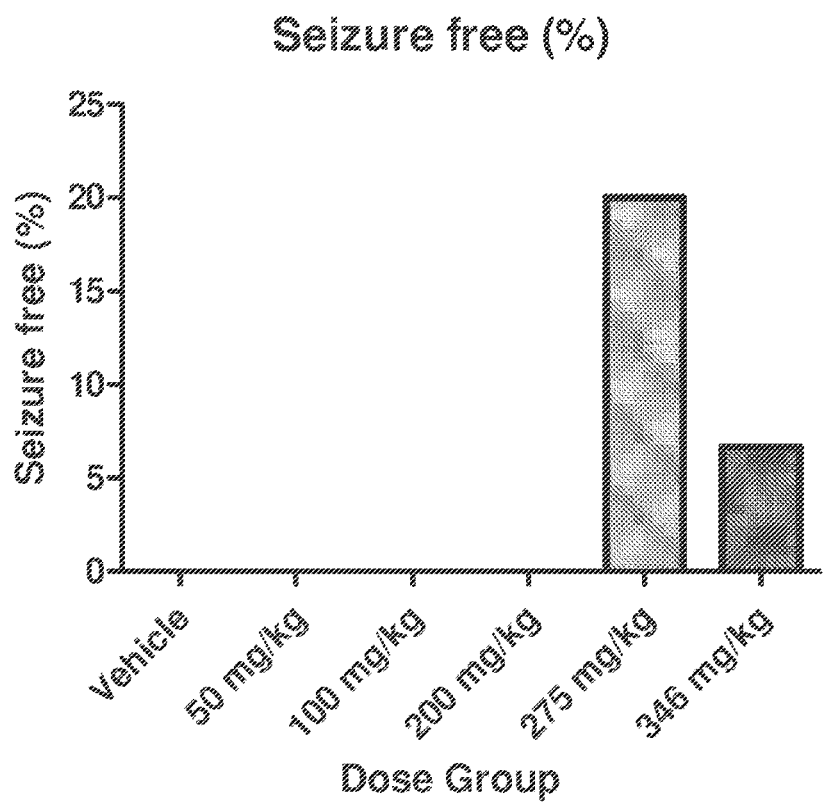
FIG. 3 shows the percentage of animals that were seizure free in the CBDV (–/–) BDS in the PTZ model of epilepsy.

FIG. 3 illustrates that although no significant effect of the CBDV (−/−) BDS was observed on the percentage of animals that were seizure free, the 275 mg/kg dose resulted in 20% of the animals becoming seizure free.

Figure 4:
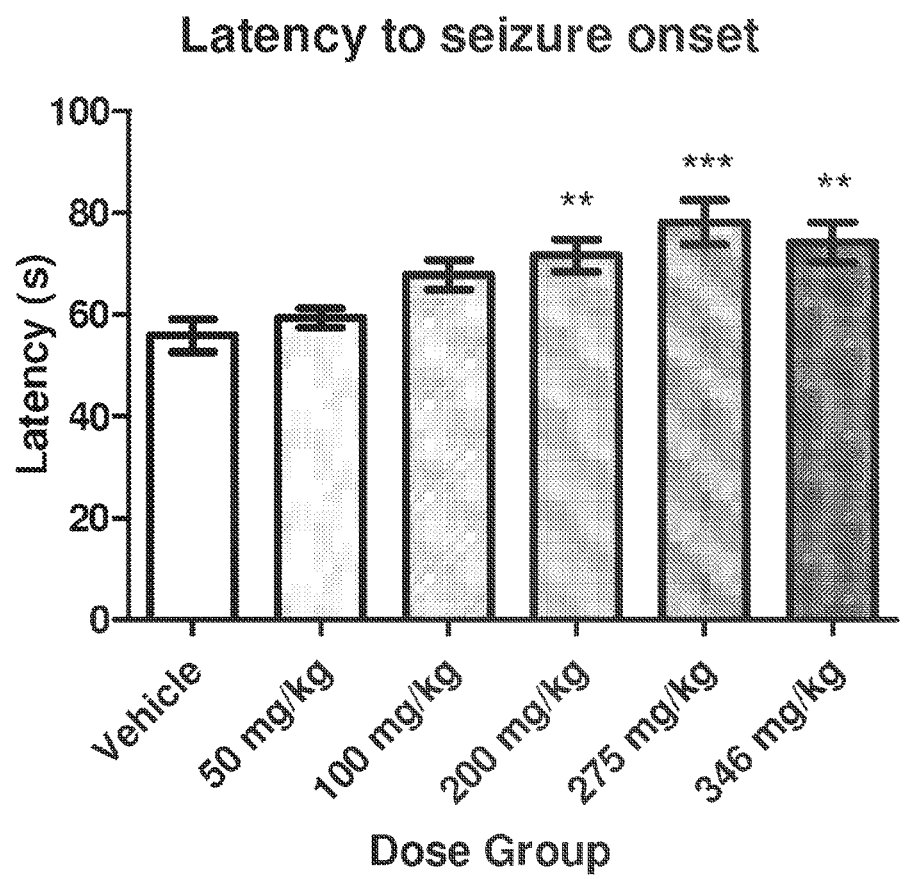
FIG. 4 shows the latency to seizure onset in the CBDV (–/–) BDS in the PTZ model of epilepsy.

FIG. 4 illustrates the latency to seizure onset was statistically increased in all of the high dose groups (200, 275 and 346 mg/kg) of the CBDV (−/−) BDS.

Figure 5:
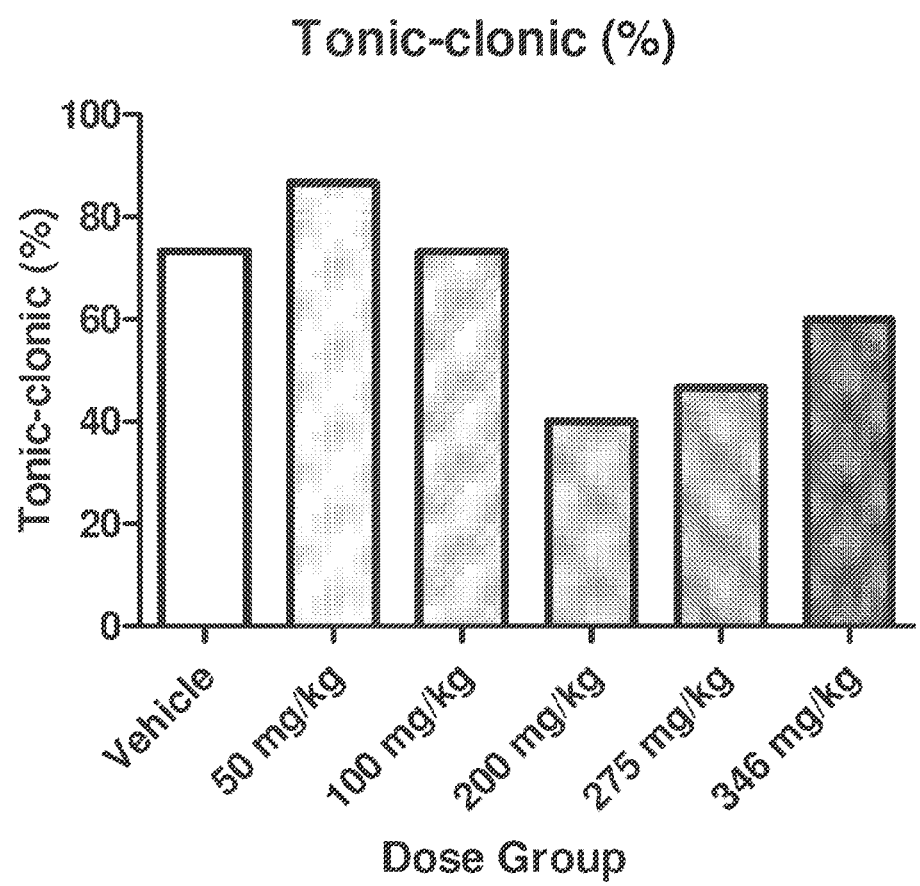
FIG. 5 shows the percentage of animals that experienced tonic-clonic seizures in the CBDV (–/–) BDS in the PTZ model of epilepsy.

FIG. 5 illustrates the percentage of animals that experienced the severe tonic-clonic seizures decreased in the higher dose groups (200, 275 and 346 mg/kg) of the CBDV (−/−) BDS; however the decrease was not statistically significant.

Conclusion:

From the above data it would appear that the CBDV (−/−) BDS composition will reduce seizure severity and mortality and increase latency to onset of seizures, making it a desirable composition for use in the treatment of epilepsy.

The omission of the cannabinoids THCV and THC from a BDS further obviates concerns associated with CB1 antagonism and psychosis.

Example 2

Analysis of CBDV (−/−) BDS

The CBDV (−/−) BDS which was used in Example 1 above can be obtained using centrifugal partition chromatography (CPC) of a CBDV (+/+) BDS.

A CBDV (−/−) BDS has been produced and analysed as described in Table 2.1 below:

TABLE 2.1

| CBDV (−/−) BDS amount in total and range | | | | |
|---|---|---|---|---|
| CBDV (−/−) BDS | Amount (% w/w) | Range (±10%) | Range (±25%) | Range (±50%) |
| CBDVA | 0.14 | 0.13-0.15 | 0.11-0.18 | 0.07-0.21 |
| CBDV | 41.19 | 37.07-45.31 | 30.89-51.49 | 20.60-61.79 |
| CBDA | 0.07 | 0.06-0.08 | 0.05-0.09 | 0.04-0.11 |
| CBG | 0.59 | 0.53-0.65 | 0.44-0.74 | 0.30-0.89 |
| CBD | 17.70 | 15.93-19.47 | 13.28-22.13 | 8.85-26.55 |
| CBCV | 4.35 | 3.92-4.79 | 3.26-5.44 | 2.18-6.53 |
| CBDV (related substances) | 2.20 | 1.98-2.42 | 1.65-2.75 | 1.10-3.30 |
| CBC | 0.93 | 0.84-1.02 | 0.70-1.16 | 0.47-1.40 |
| Total Cannabinoids | 67.17 | | | |
| Total Non-cannabinoids | 32.83 | | | |

The total phytocannabinoid containing fraction of CBDV (−/−) BDS comprises approximately 41% of the total BDS. According to variation this fraction may vary by ±10% up to ±50%.

TABLE 2.2

| Cannabidivarin (−/−) BDS by percentage cannabinoid | |
|---|---|
| CBDV (−/−) BDS | Amount (% of total cannabinoid) |
| CBDVA | 0.23 |
| CBDV | 61.30 |
| CBDA | 0.11 |
| CBG | 0.96 |
| CBD | 28.90 |
| CBCV | 7.11 |
| CBDV (related substances) | 3.60 |
| CBC | 1.52 |

The amount of the principle phytocannabinoid in the CBDV (−/−) BIDS as a percentage of the phytocannabinoid containing fraction is approximately 61%. According to variation this fraction may vary by ±10% up to ±50%.

In this Example it is intended that references be made to the principle or secondary components independently of the 'other' cannabinoids.

Comparative Example 3

CBDV (+/+) BDS Analysis

The following example is included to provide details of the components of the CBDV (+/+) BDS. The CBDV (+/+) BDS was obtained by subcritical $CO_2$ extraction. It comprises, as well as CBDV, the cannabinoids CBD, THCV and THC in significant quantities (each greater than 1% by weight as a percentage of total cannabinoid content). THC has been ascribed a pro-convulsant and it can also have marked psychoactive effects in addition to other side effects such as anxiety which are not desired. THCV whilst showing anti-convulsant activity specific to generalized seizures in epilepsy is a CB1 antagonist and following evidence to suggest that the CB1 antagonist rimonabant may cause epilepsy and other undesired effects it may be desirable to remove these cannabinoids from a BDS whilst still retaining the non-cannabinoid component(s) which may contribute to the activity of the BDS.

A CBDV (+/+) BDS can be obtained from extraction of CBDV-rich plants. Such chemovars are bred specifically to produce a significant proportion of their cannabinoids as CBDV.

The CBDV chemotype results from the breeding of plants which carry both postulated $B_0$ and $A_{PR}$ genes.

The $B_0$ gene instruct the plants to synthesize the cyclic part of the CBD molecule and the $A_{PR}$ gene instructs the plant to synthesize this molecule with a propyl side chain, as opposed to the usual pentyl chain found in CBD.

A CBDV chemovar has been bred and the BDS analysed as described in Table 3.1 below:

TABLE 3.1

| CBDV (+/+) BDS amount in total and range | | | | |
|---|---|---|---|---|
| CBDV (+/+) BDS | Amount (% w/w) | Range (±10%) | Range (±25%) | Range (±50%) |
| CBDVA | 0.14 | 0.13-0.15 | 0.11-0.18 | 0.07-0.21 |
| CBDV | 41.19 | 37.07-45.31 | 30.89-51.49 | 20.60-61.79 |
| CBDA | 0.07 | 0.06-0.08 | 0.05-0.09 | 0.04-0.11 |
| CBG | 0.59 | 0.53-0.65 | 0.44-0.74 | 0.30-0.89 |
| CBD | 17.70 | 15.93-19.47 | 13.28-22.13 | 8.85-26.55 |
| THCV | 3.06 | 2.75-6.12 | 2.30-3.83 | 1.53-4.59 |
| CBCV | 4.35 | 3.92-4.79 | 3.26-5.44 | 2.18-6.53 |
| THC | 0.88 | 0.79-0.97 | 0.66-1.10 | 0.44-1.32 |
| CBDV (related substances) | 2.20 | 1.98-2.42 | 1.65-2.75 | 1.10-3.30 |
| CBC | 0.93 | 0.84-1.02 | 0.70-1.16 | 0.47-1.40 |
| Total Cannabinoids | 71.11 | | | |
| Total Non-cannabinoids | 28.89 | | | |

The total phytocannabinoid containing fraction of CBDV (+/+) BDS comprises approximately 41% of the total BDS. According to variation this fraction may vary by ±10% up to +50%.

TABLE 3.2

CBDV (+/+) BDS by percentage cannabinoid

| CBDV (+/+) BDS | Amount (% of total cannabinoid) |
|---|---|
| CBDVA | 0.20 |
| CBDV | 57.92 |
| CBDA | 0.10 |
| CBG | 0.83 |
| CBD | 24.89 |
| THCV | 4.30 |
| CBCV | 6.12 |
| THC | 1.24 |
| CBDV (related substances) | 3.09 |
| CBC | 1.31 |

The amount of the principle phytocannabinoid in the CBDV (+/+) BDS as a percentage of the phytocannabinoid containing fraction is approximately 58%. According to variation this fraction may vary by ±10% up to ±50%.

In this Example it is intended that references be made to the principle or secondary components independently of the 'other' cannabinoids.

Comparative Example 4

Non-Cannabinoid Profile of a High Phytocannabinoid Containing Plant

This comparative Example is included to demonstrate a typical terpene profile obtained from a cannabis plant that has been bred to produce a high quantity of cannabinoids.

The non-cannabinoid components of a phytocannabinoid BDS may play an important role in the BDS's pharmacology. As such the terpene profile is classified below. The following tables illustrate the terpene profile of a CBD chemovar which is representative of a high phytocannabinoid containing plant. Five plants were freshly harvested and extracted using steam distillation. The principle monoterpene and sesquiterpene are highlighted in bold.

TABLE 4.1

Monoterpene amount by percentage of total terpene fraction and ranges

| Monoterpenes | Amount (% of terpene fraction) | Range (±10%) | Range (±25%) | Range (±50%) |
|---|---|---|---|---|
| Pinene (alpha & beta) | 10.56 | 9.50-11.62 | 7.92-13.20 | 5.28-15.84 |
| Myrcene | 39.46 | 35.51-43.41 | 29.60-49.33 | 19.73-59.19 |
| Limonene | 4.14 | 3.73-4.55 | 3.11-5.18 | 2.07-6.21 |
| Beta-ocimene | 4.04 | 3.64-4.44 | 3.03-5.05 | 2.02-6.06 |
| Total | 58.20 | | | |

The monoterpene containing fraction comprises approximately 52-64% (w/w) of the total terpene fraction.

TABLE 4.2

Monoterpene amount by percentage of monoterpenes

| Monoterpenes | Amount (% of monoterpene fraction) |
|---|---|
| Pinene (alpha & beta) | 18.14 |
| Myrcene | 67.80 |
| Limonene | 7.12 |
| Beta-ocimene | 6.94 |

The amount of the principle monoterpene myrcene in the monoterpene fraction as a percentage of the monoterpene fraction is approximately 61-75% (w/w). The monoterpene fraction also has a secondary monoterpene pinene which is present at approximately 16.3-20% (w/w) of the monoterpene fraction.

TABLE 4.3

Sesquiterpene amount by percentage of total terpene fraction and ranges

| Sesquiterpenes | Amount (% of terpene fraction) | Range (±10%) | Range (±25%) | Range (±50%) |
|---|---|---|---|---|
| Caryophyllenes (t & oxide) | 29.27 | 26.34-32.20 | 21.95-36.59 | 14.64-43.91 |
| Bergotamene | 0.18 | 0.16-0.20 | 0.14-0.23 | 0.09-0.27 |
| Humulene | 7.97 | 7.17-8.77 | 5.98-9.96 | 3.99-11.96 |
| Aromadendrene | 0.33 | 0.30-0.36 | 0.25-0.41 | 0.17-0.50 |
| Selinene | 0.59 | 0.53-0.65 | 0.44-0.74 | 0.30-0.89 |
| Anon | 0.44 | 0.40-0.48 | 0.33-0.55 | 0.22-0.66 |
| Farnesene (Z, E & alpha) | 1.55 | 1.40-1.71 | 1.16-1.94 | 0.78-2.33 |
| alpha Gurjunene | 0.12 | 0.11-0.13 | 0.09-0.15 | 0.06-0.18 |
| Bisabolene | 0.39 | 0.35-0.43 | 0.29-0.49 | 0.20-0.59 |
| Nerolidol | 0.43 | 0.39-0.47 | 0.32-0.54 | 0.22-0.65 |
| Diepicedrene-1-oxide | 0.38 | 0.34-0.42 | 0.29-0.48 | 0.19-0.57 |
| Alpha-Bisabolol | 0.16 | 0.14-0.18 | 0.12-0.20 | 0.08-0.24 |
| Total | 41.80 | | | |

The sesquiterpene containing fraction comprises approximately 27-32 (w/w) of the total terpene fraction.

TABLE 4.4

Sesquiterpene amount by percentage of sesquiterpenes

| Sesquiterpenes | Amount (% of sesquiterpene fraction) |
|---|---|
| Caryophyllenes (t & oxide) | 70.02 |
| Bergotamene | 0.43 |
| Humulene | 19.07 |
| Aromadendrene | 0.79 |
| Sellnene | 1.41 |
| Anon | 1.05 |
| Farnesene (Z, E & alpha) | 3.71 |
| alpha Gurjunene | 0.29 |
| Bisabolene | 0.93 |
| Nerolidol | 1.03 |
| Diepicedrene-1-oxide | 0.91 |
| Alpha-Bisabolol | 0.38 |

Comparative Example 5

Non-Cannabinoid Profile of a 'zero Cannabinoid' Plant

This comparative Example describes the terpene profile of a different cannabis plant to that described oi Example 4 above and is reproduced here for comparative purposes.

Patent application number PCT/GB2008/001837 describes the production of a 'zero cannabinoid' plant. These plants were produced by selective breeding to produce a *Cannabis sativa* L plant that contained a generally qualitatively similar terpene profile as a *Cannabis sativa* L plant that produced cannabinoids yet it was devoid of any cannabinoids. These plants can be used to produce cannabinoid-free plant extracts which are useful control plants in experiments and clinical trials. A breakdown of the terpene profile produced in the plants can be found in the table below. The primary monoterpenes and sesquiterpene are highlighted in bold.

TABLE 5.1

Monoterpene amount by percentage of total terpene traction and ranges

| Monoterpenes | Amount (% of terpene fraction) | Range (±10%) | Range (±25%) | Range (±50%) |
|---|---|---|---|---|
| Pinene (alpha & beta) | 29.34 | 26.41-32.27 | 22.01-36.68 | 14.67-44.01 |
| Myrcene | 29.26 | 26.33-32.19 | 21.95-36.58 | 14.63-43.89 |
| Limonene | 5.32 | 4.79-5.85 | 3.99-6.65 | 2.66-7.98 |
| Linalol | 4.50 | 4.05-4.95 | 3.38-5.63 | 2.25-6.75 |
| Verbenol (cis & trans) | 3.45 | 3.11-3.80 | 2.59-4.31 | 1.73-5.18 |
| Total | 71.87 | | | |

The monoterpene containing fraction comprises approximately 65-79% (w/w) of the total terpene fraction.

TABLE 5.2

Monoterpene amount by percentage of monoterpenes

| Monoterpenes | Amount (% of monoterpene fraction) |
|---|---|
| Pinene (alpha & beta) | 40.82 |
| Myrcene | 40.71 |
| Limonene | 7.41 |
| Linalol | 6.26 |

TABLE 5.3

Sesquiterpene amount by percentage of total terpene fraction and ranges

| Sesquiterpenes | Amount (% of terpene fraction) | Range (±10%) | Range (±25%) | Range (±50%) |
|---|---|---|---|---|
| Caryophyllenes (t & oxide) | 10.89 | 9.80-11.98 | 8.17-13.61 | 5.45-16.34 |
| Bergotamene | 2.51 | 2.26-2.76 | 1.88-3.14 | 1.26-3.77 |
| Farnesene (Z, E & alpha) | 3.43 | 3.09-3.77 | 2.57-4.29 | 1.72-5.15 |
| Humulene (& epoxide II) | 5.04 | 4.54-5.54 | 3.78-6.30 | 2.52-7.56 |
| delta guaiene | 2.40 | 2.16-2.64 | 1.80-3.00 | 1.20-3.60 |
| Bisabolene | 3.85 | 3.47-4.24 | 2.89-4.81 | 1.93-5.78 |
| Total | 28.12 | | | |

The sesquiterpene containing fraction comprises approximately 25-31% (w/w) of the total terpene fraction.

TABLE 5.4

Sesquiterpene amount by percentage of sesquiterpenes

| Sesquiterpenes | Amount (% of sesquiterpene fraction) |
|---|---|
| Caryophyllenes (t & oxide) | 38.73 |
| Bergotamene | 8.93 |
| Farnesene (Z, E & alpha) | 12.20 |
| Humulene (& epoxide II) | 17.92 |
| delta guaiene | 8.53 |
| Bisabolene | 13.69 |

The amount of the principle sesquiterpene caryophyllene in the sesquiterpene fraction as a percentage of the sesquiterpene fraction is approximately 35-43% (w/w). The sesquiterpene fraction also has a secondary sesquiterpene humulene which is present at approximately 16-20% (w/w) of the sesquiterpene fraction.

Comparative Example 6

Use of CBDV (+/+) BDS in the PTZ Model of Generalised Seizures

This comparative Example was previously presented in GB1005364.3 (unpublished) patent application and is included here for representative purposes.

Methodology as described in Example 1.

CBDV (+/+) BDS was administered at four doses that yielded a dose of CBDV of 50 and 100 mg/kg. Table 6.1 below details the data obtained.

TABLE 5.1

| CBDV (+/+) BDS (mg/kg) | Mortality (%) |
|---|---|
| 0 | 26.3 |
| 50 | 16.7 |
| 100 | 0 |

As can be seen the CBDV (+/+) BDS exhibited a trend to decrease seizure-related mortality.

REFERENCES

ALGER, B. E. (2006) Not too excited? Thank your endocannabinoids. *Neuron*, 51, 393-5.

AMES F R. (1986) Anticonvulsant effect of cannabidiol. *South African Medical Journal* 69:14.

AVOLI, M., LOUVEL, J., PUMAIN, R. & KOHLING, R. (2005) Cellular and molecular mechanisms of epilepsy in the human brain. *Prog Neurobiol.*

BOSTANCI, M. O. & BAGIRICI, F. (2006) The effects of octanol on penicillin induced epileptiform activity in rats: an in vivo study. *Epilepsy Res*, 71, 188-94.

BRUST, J. C., NG, S. K., HAUSER, A. W. & SUSSER, M. (1992) Marijuana use and the risk of new onset seizures. *Trans Am Clin Climatol Assoc*, 103, 176-81.

CONSROE, P. F., WOOD, G. C. & BUCHSBAUM, H. (1975) Anticonvulsant Nature of Marihuana Smoking. *J. American Medical Association* 234 306-307

CUNHA, J. M., CARLINI, E. A., PEREIRA, A. E., RAMOS, O. L., PIMENTEL, C., GAGLIARDI, R., SANVITO, W. L., LANDER, N. & MECHOULAM, R. (1980) Chronic administration of cannabidiol to healthy volunteers and epileptic patients. *Pharmacology*, 21, 175-85.

DAVIS, M. I., RONESI, J. & LOVINGER, D. M. (2003) A Predominant Role for Inhibition of the Adenylate Cyclase/Protein Kinase A Pathway in ERK Activation by Cannabinoid Receptor 1 in N1E-115 Neuroblastoma Cells. *J. Biol. Chem.*, 278, 48973-48980.

DREIFUSS, F. E., BANCAUD, J., HENRIKSEN, O., RUBIO-DONNADIEU, F. PENRY, J. K. & SEINO, M. (1981) Proposal for revised clinical and electroencephalographic classification of epileptic seizures. *Epilepsia*, 22, 489-501.

FERDINAND, R. F., VAN DER ENDE, J., BONGERS, I., SELTEN, J. P., HUIZINK, A. & VERHULST, F. C. (2005) Cannabis-psychosis pathway independent of other types of psychopathology. *Schizophr Res*, 79, 289-95.

FISHER, R. S., VICKREY, B. G., GIBSON, P., HERMANN, B., PENOVICH, P., SCHERER, A. & WALKER, S. (2000) The impact of epilepsy from the patient's perspective I. Descriptions and subjective perceptions. *Epilepsy Res*, 41, 39-51.

GASTAUT, H. (1970) Clinical and Electroencephalographical Classification of Epileptic Seizures. *Epilepsia*, 11, 102-112.

LUTZ, B. (2004) On-demand activation of the endocannabinoid system in the control of neuronal excitability and epileptiform seizures. *Biochem Pharmacol*, 68, 1691-8.

MACKIE, K. (2006) Cannabinoid receptors as therapeutic targets. *Annu Rev Pharmacol Toxicol*, 46, 101-22.

MCCORMICK, D. A. & CONTRERAS, D. (2001) On the cellular and network bases of epileptic seizures. *Annu Rev Physiol*, 63, 815-46.

MERLIS, J. K. (1970) Proposal for an International Classification of the Epilepsies. *Epilepsia*, 11, 114-119.

NG et al. (1990) Illicit drug use and the risk of new-onset seizures, *American Journal of Epidemiology* 132: 47-57.

OBAY, B. D., TASDEMIR, E., TUMER, C., BILGIN, H. M. & SERMET, A. (2007) Antiepileptic effects of ghrelin on pentylenetetrazole-induced seizures in rats. *Peptides*, 28, 1214-9.

PEREIRA, M. B., FREITAS, R. L., ASSIS, M. A., SILVA, R. F., FONTELES, M. M., FREITAS, R. M. & TAKAHASHI, R. N. (2007) Study pharmacologic of the GABAergic and glutamatergic drugs on seizures and status epilepticus induced by pilocarpine in adult Wistar rats. *Neurosci Lett*, 419, 253-7.

PERTWEE R. G., (2000) Cannabinoid receptor ligands: clinical and neuropharmacological considerations, relevant to future drug discovery and development Exp. Opin. Invest. Drugs 9(7):

RAUCA, C., WISWEDEL, I., ZERBE, R., KEILHOFF, G. & KRUG, M. (2004) The role of superoxide dismutase and alpha-tocopherol in the development of seizures and kindling induced by pentylenetetrazol—influence of the radical scavenger alpha-phenyl-N-tert-butyl nitrone. *Brain Res*, 1009, 203-12.

SANDER, J. W. (2003) The epidemiology of epilepsy revisited. *Curr Opin Neurol*, 16, 165-70.

SWANN, J. W. (2004) The effects of seizures on the connectivity and circuitry of the developing brain. *Ment Retard Dev Disabil Res Rev*, 10, 96-100.

TREMBLY B. SHERMAN M. (1990) Double-blind clinical study of cannabidiol as a secondary anticonvulsant. Marijuana '90 International Conference on Cannabis and Cannabinoids. Kolympari, Crete, Jul. 8-11, 1990.

WINGERCHUK, D. (2004) Cannabis for medical purposes: cultivating science, weeding out the fiction. *Lancet*, 364, 315-6.

The invention claimed is:

1. A composition comprising the phytocannabinoids cannabidivarin (CBDV) and cannabidiol (CBD), wherein the CBDV and CBD are present in a ratio of from 7:1 to 1:2 (CBDV:CBD).

2. A composition as claimed in claim 1, further comprising one or more excipients.

3. A composition as claimed in claim 1, which further comprises at least one non-cannabinoid component of cannabis.

4. A composition as claimed in claim 3, wherein the at least one non-cannabinoid component of cannabis is or comprises a terpene.

5. A composition as claimed in claim 1, wherein the phytocannabinoids comprise, or consist essentially of CBDV, CBD and one or more cannabichromene type compounds.

6. A composition as claimed in claim 5, wherein the one or more cannabichromene type compounds is cannabichromene propyl variant (CBCV) and/or cannabichromene (CBC).

7. A composition as claimed in claim 1, which is absent or substantially absent of any other cannabinoids.

8. A composition as claimed in claim 7, wherein the any other cannabinoids are tetrahydrocannabivarin (THCV) and/or tetrahydrocannabinol (THC).

9. A composition as claimed in claim 1, wherein a unit dosage form comprises from 500 to 2000 mg CBDV.

10. A composition as claimed in claim 1, wherein a unit dosage form comprises from 100 to 600 mg CBD.

11. A composition as claimed in claim 1, further comprising a standard anti-epileptic drug (SAED).

12. A composition consisting essentially of the phytocannabinoids cannabidivarin (CBDV) and cannabidiol (CBD), wherein the CBDV and CBD are present in a ratio of from 7:1 to 1:2 (CBDV:CBD).

13. A composition as claimed in claim 12, further comprising one or more excipients.

14. A composition as claimed in claim 12, which further comprises at least one non-cannabinoid component of cannabis.

15. A composition as claimed in claim 14, wherein the at least one non-cannabinoid component of cannabis is or comprises a terpene.

16. A composition as claimed in claim 12, wherein the phytocannabinoids comprise, or consist essentially of CBDV, CBD and one or more cannabichromene type compounds.

17. A composition as claimed in claim 16, wherein the one or more cannabichromene type compounds is cannabichromene propyl variant (CBCV) and/or cannabichromene (CBC).

18. A composition as claimed in claim 12, which is absent or substantially absent of any other cannabinoids.

19. A composition as claimed in claim 18, wherein the any other cannabinoids are tetrahydrocannabivarin (THCV) and/or tetrahydrocannabinol (THC).

20. A composition as claimed in claim 12, wherein a unit dosage form comprises from 500 to 2000 mg CBDV.

21. A composition as claimed in claim 12, wherein a unit dosage form comprises from 100 to 600 mg CBD.

22. A composition as claimed in claim 12, further comprising a standard anti-epileptic drug (SAED).

* * * * *